(12) United States Patent
Revaud et al.

(10) Patent No.: US 9,987,351 B2
(45) Date of Patent: Jun. 5, 2018

(54) LENTIVIRAL VECTORS FOR GENERATING IMMUNE RESPONSES AGAINST HUMAN T LYMPHOTROPHIC VIRUS TYPE 1

(71) Applicant: THERAVECTYS, Paris (FR)

(72) Inventors: Deborah Revaud, Mondeville (FR); Cecile Bauche, Paris (FR)

(73) Assignee: THERAVECTYS, Paris (FR)

( * ) Notice: Subject to any disclaimer, the term of this patent is extended or adjusted under 35 U.S.C. 154(b) by 0 days. days.

(21) Appl. No.: 15/112,854

(22) PCT Filed: Jan. 27, 2015

(86) PCT No.: PCT/IB2015/050598
§ 371 (c)(1),
(2) Date: Jul. 20, 2016

(87) PCT Pub. No.: WO2015/111024
PCT Pub. Date: Jul. 30, 2015

(65) Prior Publication Data
US 2016/0331831 A1 Nov. 17, 2016

(30) Foreign Application Priority Data
Jan. 27, 2014 (EP) .................................... 14290009

(51) Int. Cl.
| | | |
|---|---|---|
| *A61K 39/21* | (2006.01) | |
| *A61K 39/12* | (2006.01) | |
| *C07K 14/05* | (2006.01) | |
| *C07K 14/15* | (2006.01) | |
| *C07K 14/005* | (2006.01) | |
| *C12N 7/00* | (2006.01) | |
| *C12N 15/86* | (2006.01) | |
| *A61K 39/00* | (2006.01) | |

(52) U.S. Cl.
CPC .............. *A61K 39/21* (2013.01); *A61K 39/12* (2013.01); *C07K 14/005* (2013.01); *C07K 14/15* (2013.01); *C12N 7/00* (2013.01); *C12N 15/86* (2013.01); *A61K 2039/5258* (2013.01); *A61K 2039/53* (2013.01); *C12N 2740/14022* (2013.01); *C12N 2740/14034* (2013.01); *C12N 2740/14071* (2013.01); *C12N 2740/15023* (2013.01); *C12N 2740/15034* (2013.01); *C12N 2740/15043* (2013.01)

(58) Field of Classification Search
None
See application file for complete search history.

(56) References Cited

FOREIGN PATENT DOCUMENTS

| WO | WO 2004/016228 | * | 2/2004 |
|---|---|---|---|
| WO | 2009/019612 A2 | | 2/2009 |
| WO | 2011/000860 A2 | | 1/2011 |

OTHER PUBLICATIONS

Dekaban et al., Virology, 2000, 274:86-93.*
Rowan et al., Leukemia Research and Treatment, 2012, 7 pages.*
Rowan et al.; "Is There a Role for HTLV-1-Specific CTL in Adult T-Cell Leukemia/Lymphoma?"; Leukemia Research and Treatment, vol. 2012, Jan. 1, 2012, pp. 1-7.
Hu et al.; "Immunization Delivered by Lentiviral Vectors for Cancer and Infectious Diseases"; Immunological Reviews, vol. 239, Jan. 2011, pp. 45-61.
Valeri et al.; "Requirement of the human T-cell leukemia virus p12 and p30 products for infectivity of human dendritic cells and macaques but not rabbits"; Blood, vol. 116, No. 19, Nov. 11, 2010, pp. 3809-3817.
Bai et al.; "Overview on HTLV-1 p12, p8, p30, p13: accomplices in persistent infection and viral pathogenesis"; Frontiers in Microbiology, vol. 3, Dec. 11, 2012, pp. 1-9.
"Human T-Cell Lymphotropic Virus Type 1"; International Agency for Research on Cancer (IARC) Working Group, 1996, pp. 315-340.
Lairmore et al.; "Molecular Determinants of Human T-lymphotropic Virus Type 1 Transmission and Spread"; Viruses, vol. 3, No. 12, Jul. 1, 2011, pp. 1131-1165.

* cited by examiner

*Primary Examiner* — Nicole Kinsey White
(74) *Attorney, Agent, or Firm* — Whitham, Curtis & Cook, P.C.

(57) ABSTRACT

The present invention relates to compositions, methods, and uses employing lentiviral vector particles for induction of an immune response by administration to a human, wherein the lentiviral vector particles comprise a lentiviral vector, wherein the DNA of the lentiviral vector comprises a promoter directing expression of a HTLV-1 p12p30-Tax-HBZ fusion protein. The invention encompasses these vectors, methods of making the vectors, and methods of using them, including medicinal uses.

12 Claims, 7 Drawing Sheets

Figure 1

LENTIVIRAL VECTORS FOR GENERATING IMMUNE RESPONSES AGAINST HUMAN T LYMPHOTROPHIC VIRUS TYPE 1

TECHNICAL FIELD

The present invention is in the field of recombinant vaccine technology and relates to improvements of lentiviral vectors, which can be used to generate immune responses in patients infected with Human T Lymphotropic Virus Type 1 (HTLV-1). The vectors provide improved immune responses over other vectors.

BACKGROUND

Recombinant vaccines have been developed with the progress of recombinant DNA technology, allowing the modification of viral genomes to produce modified viruses. In this manner, it has been possible to introduce genetic sequences into non-pathogenic viruses, so that they encode immunogenic proteins to be expressed in target cells upon infection or transduction, in order to develop a specific immune response in their host.

Such vaccines constitute a major advance in vaccine technology (Kutzler et al., Nat Rev Genet, 9(10): 776-788, 2008). In particular, they have the advantage over traditional vaccines of avoiding live (attenuated) virus and eliminating risks associated with the manufacture of inactivated vaccines.

Gene delivery using modified retroviruses (retroviral vectors) was introduced in the early 1980s by Mann et al. (*Cell*, 33(1):153-9, 1983). The most commonly used oncogenic retroviral vectors are based on the Moloney murine leukemia virus (MLV). They have a simple genome from which the polyproteins Gag, Pol and Env are produced and are required in trans for viral replication (Breckpot et al., 2007, *Gene Ther*, 14(11):847-62; He et al. 2007, *Expert Rev vaccines*, 6(6):913-24). Sequences generally required in cis are the long terminal repeats (LTRs) and its vicinity: the inverted repeats (IR or att sites) required for integration, the packaging sequence ψ the transport RNA-binding site (primer binding site, PBS), and some additional sequences involved in reverse transcription (the repeat R within the LTRs, and the polypurine tracts, PPT, necessary for plus strand initiation). To generate replication-defective retroviral vectors, the gag, pol, and env genes are generally entirely deleted and replaced with an expression cassette.

Retroviral vectors deriving from lentivirus genomes (i.e. lentiviral vectors) have emerged as promising tools for both gene therapy and immunotherapy purposes, because they exhibit several advantages over other viral systems. In particular, lentiviral vectors themselves are not toxic and, unlike other retroviruses, lentiviruses are capable of transducing non-dividing cells, in particular dendritic cells (He et al. 2007, *Expert Rev vaccines*, 6(6):913-24), allowing antigen presentation through the endogenous pathway.

Lentiviruses are linked by similarities in genetic composition, molecular mechanisms of replication and biological interactions with their hosts. They are best known as agents of slow disease syndromes that begin insidiously after prolonged periods of subclinical infection and progress slowly; thus, they are referred to as the "slow" viruses (Narayan et al., 1989, *J Gen Virol*, 70(7):1617-39). They have the same basic organization as all retroviruses but are more complex due to the presence of accessory genes (e.g., vif, vpr, vpu, nef, tat, and rev), which play key roles in lentiviral replication in vivo.

Lentiviruses represent a genus of slow viruses of the Retroviridae family, which includes the human immunodeficiency viruses (HIV), the simian immunodeficiency virus (SIV), the equine infectious encephalitis virus (EIAV), the caprine arthritis encephalitis virus (CAEV), the bovine immunodeficiency virus (BIV) and the feline immunodeficiency virus (FIV). Lentiviruses can persist indefinitely in their hosts and replicate continuously at variable rates during the course of the lifelong infection. Persistent replication of the viruses in their hosts depends on their ability to circumvent host defenses.

The design of recombinant integrating lentiviral vectors is based on the separation of the cis- and trans-acting sequences of the lentivirus. Efficient transduction in non-dividing cells requires the presence of two cis-acting sequences in the lentiviral genome, the central polypurine tract (cPPT) and the central termination sequence (CTS). These lead to the formation of a triple-stranded DNA structure called the central DNA "flap", which maximizes the efficiency of gene import into the nuclei of non-dividing cells, including dendritic cells (DCs) (Zennou et al., 2000, Cell, 101(2) 173-85; Arhel et al., 2007, *EMBO J*, 26(12): 3025-37).

Dendritic cells are of primary importance for antigen presentation because they constitute the main class of antigen presenting cells (APCs) whose primary function is to present antigens and initiate an immune response.

To generate an immune response, antigenic proteins must be processed by cells into peptides that are displayed on the cell surface by major histocompatibility complex proteins (MHCs). Circulating APCs present the peptide-MHC complexes to T cells in the draining lymph nodes, where they interact with T cell receptors, and, in conjunction with co-stimulatory signals, activate the T cells.

A variety of studies have shown that inoculation with lentiviral vectors leads to antigen presentation by DCs and strong activation of antigen specific cytotoxic T lymphocytes (CTLs; $CD8^+$ T cells). Therefore, lentiviral vectors have been engineered for the last 10 years for gene transfer and immunotherapy applications.

The vectors routinely contain strong constitutive promoters containing enhancers, such as the CMV promoter. Michelini et al., Vaccine 27(34):4622-29 (2009); Karwacz et al., J. Virol. 83(7):30943103 (2009); Negri et al., Molecular Therapy 15(9):1716-23 (2007); and Buffa et al., J. General Virology 87:1625-1634 (2006).

Lentiviral vectors have been improved in their safety by removal of the LTR U3 sequence, resulting in "self-inactivating" vectors that are entirely devoid of viral promoter and enhancer sequences originally present within the LTRs.

The lentiviral particles, which contain lentiviral vectors, can be produced by recombinant technology upon transient transfection of cells, for example HEK 293T human cultured cells, by different DNA plasmids:

(i) a packaging plasmid, which expresses at least the Gag, Pol Rev, Tat and, in some cases, structural and enzymatic proteins necessary for the packaging of the transfer construct;

(ii) a proviral transfer plasmid, containing an expression cassette and HIV cis-acting factors necessary for packaging, reverse transcription, and integration; and (iii) an envelope-encoding plasmid, in most cases the glycoprotein of vesicular stomatitis virus (VSV.G), a protein that allows the formation of mixed particles (pseudotypes) that can target a wide variety of cells, especially major histocompatibility (MHC) antigen-presenting cells (APCs), including DCs.

This procedure allows obtaining transient production of lentiviral particle vectors by the transfected cells. However, the lentiviral particle vectors may also be continuously produced by cells by stably inserting the packaging genes, the proviral coding DNA, and the envelope gene into the cellular genome. This allows the continuous production of lentiviral particle vectors by the cells without the need for transient transfection. Of course, a combination of these procedures can be used, with some of the DNAs/plasmids integrated into the cellular genome and others provided by transient transfection.

Non-integrating lentiviral vectors have been designed. Examples of non-integrating lentiviral vectors are provided in Coutant et al., PLOS ONE 7(11):e48644 (2102), Karwacz et al., J. Virol. 83(7):3094-3103 (2009), Negri et al., Molecular Therapy 15(9):1716-1723 (2007); Hu et al., Vaccine 28:6675-6683 (2010).

Deletion in the U3 region of the 3' LTR of the viral promoter and enhancer sequences in self-inactivating lentiviral vectors limits the likelihood of endogenous promoter activation. These concerns with safety directly address the experiences gained from the SCID-X1 gene therapy trial carried out in 1998-1999, performed with Moloney virus-based retroviral vectors on children suffering from a rare form of X-linked (SCID-X1 gene) severe immunodeficiency disease (Cavazzana-Calvo et al., 2000, Science., 288(5466): 669-72). During this trial, four of nine children developed leukemia as a result of the integration of the Moloney-derived retroviral vector at close proximity to the human LMO2 proto-oncogene (Hacein-Bey-Abina et al., 2008, J.Clin.Invest., 118(9):3132-3142). It was demonstrated that malignancy was the consequence of the proximity of the viral U3 promoter/enhancer to the LMO2 proto-oncogene. As a result, safety is a major concern for the administration of lentivectors to humans.

Promoters can contain enhancers, which are cis-acting sequences that can act as transcriptional activators at a distance. Promoters containing enhancers have been widely employed in viral derived vectors because they appear to be the most efficient for obtaining transgene strong expression in a variety of cell types (Chinnasamy et al., 2000, Hum Gene Ther 11(13):1901-9; Rouas et al., 2008, Cancer Gene Ther 9(9):715-24; Kimura et al., 2007, Mol Ther 15(7): 1390-9; Gruh et al., 2008, J Gene Med 10(1) 21-32). However, given the safety issue of insertional mutagenesis, transcriptional enhancer sequences should be deleted from the lentiviral vector constructs to abolish the risk of insertional mutagenesis by enhancer proximity effect. This enhancer proximity effect is by far the most frequent mechanism of insertional mutagenesis and is the only effect described in human or animal cases of tumorigenic events after gene transfer.

Thus, there is a need to develop retroviral, particularly lentiviral vectors, which do not include viral enhancers, but still allow sufficient expression of transgenes encoding immunogenic peptide s, if possible, as much expression as that observed when using the CMV promoter.

Recent studies has reported on the replacement of viral promoters by DC-specific promoters deriving from major histocompatibility complex class II genes (MHC class II) (Kimura et al., 2007, Mol Ther 15(7):1390-9) and dectin-2 genes (Lopes et al., 2008, J Virol 82(1):86-95). The dectin-2 gene promoter used in Lopes et al. contains a putative enhancer and an adenoviral conserved sequence (inverted terminal repeats in adenovirus promoter) (Bonkabara et al., 2001, J. Immunology, 167:6893-6900). The MHC class II gene promoter used by Kimura et al. does not contain any known enhancer.

Yet, without an enhancer, the MHC class II promoter was found not to provide sufficient transgene expression in DCs, when administered intravenously. In particular, lentiviral vectors including MHC class II promoters did not provoke an immune reaction in immunocompetent C57BL/6 mice, in contrast to the immune responses observed with CMV promoters/enhancers. Although integration and persistent transgene expression were observed after injection in mice, the lentiviral vectors transcribed through MHC class II promoters failed to stimulate an antigen-specific CD8+ cytotoxic T-lymphocyte response, even after vaccination boost. The authors of these studies therefore concluded that the use of MHC class II promoters was of interest only for applications where persistence of expression is sought as in gene replacement therapy, but not in the context of immunotherapy. Of note, MHC class II promoters are expressed poorly in most cell types.

Thus, the MHC class II promoter is not an adequate promoter for lentiviral vectors for induction of an immune response against an antigen via IV injection. Moreover, the dectin-2 promoter is expressed poorly in most cell types and appears to contain an enhancer. Thus, the dectin-2 promoter is not a good promoter for lentiviral vectors for safety reasons.

Preferably, in immunotherapy, lentiviral vectors provide effective expression of the transgene that elicits a desired specific immune response. This requires that the expression is at a high level in APCs, such as dendritic cells.

It is also preferable that the cells transduced by the lentiviral vectors are eliminated by the immune response to provide a higher degree of safety. That is, the immune response generated against the transgene can elicit an immune response in the host sufficient to eliminate the cells that are transduced by the lentiviral vectors. The elimination of transduced cells eliminates the persistence of the lentiviral vector in the host, and possible secondary effects of the vector. In order for the transduced cells to be eliminated, expression is required in non-dendritic cells at a level that allows elimination by the immune response. Thus, appropriate expression of an antigen is desirable.

At the same time, the promoter should maximize immune stimulation through the key cells (i.e., dendritic cells) involved in the activation of naïve and memory T cells, and should minimize the risk of insertional mutagenesis and genotoxicity in stem cells, leading to malignancies. Thus, the promoter should have sufficiently high activity in dendritic and other cells, but not contain an enhancer. Based on these criteria, viral promoters, such as the CMV promoter, are not ideal because of the presence of strong enhancers. These criteria are summarized as follows:

1. high expression in antigen presenting cells, including dendritic cells, to induce maximal immune responses;
2. expression in other transduced cell types sufficient for elimination by the induced immune response; and
3. lack of an enhancer element to avoid insertional effects.

Human T Lymphotrophic Virus type 1 (HTLV-1) is the etiologic agent of Adult T-cell Leukemia/Lymphoma (ATL) (Poiesz, et al., 1980, Proc. Natl. Acad. Sci. USA, 77(12): 7415-7419; Yoshida, et al, 1982, Proc. Natl. Acad. Sci. USA, 79:2031-2035). HTLV-1 is also causatively associated with other pathologies for which there is no cure or effective treatment: myelopathy/tropical spastic paraparesis (HAM/TSP), an inflammatory chronic meningomyelitis of the grey and white matter in the spinal cord with perivascular demyelination and axonal degeneration; and uveitis and autoimmune conditions. One agent, HTLV-1, is thus responsible of at least two diseases (ATL and HAM/TSP); infected individuals never develop both.

20 million of individuals worldwide are estimated to be infected by HTLV-1, with determined endemic areas (i.e. Japan, some African countries, the Caribbean islands and Central and South America) and different virus subtypes whose predominant, cosmopolitan subtype A, shows a low genetic variability (Gessain and Cassar, 2012, *Front. Microbiol*, 3:388). However, the estimated lifetime risk for HTLV-1 infected people to develop ATL and inflammatory chronic diseases (HAM/TSP) is lower than 5%, usually 20-30 years after the onset of infection. The majority of infected people remaining asymptomatic carriers, deciphering HTLV-1 pathogenesis mechanisms is a matter of concern.

ATL is a malignant lymphoproliferative disease which has been classified into four subtypes: smoldering, chronic, lymphoma and acute (Shimoyama, 1991, *Br. J. Haematology*, 79(3):428-437). Classification is performed according to the following criteria: lymphocyte counts, percentage of atypical lymphocytes, lactate dehydrogenase (LDH) level, calcium level and skin lesions. A fifth state is also sometimes referred to, "pre-ATL", that is characterized by an asymptomatic disease with presence of abnormal peripheral blood lymphocytes with typical ATL morphology. ATL cells have indeed a so-called "flower cells" aspect with condensed chromatin, small or absent nuclei and agranular and basophil cytoplasm.

Patients developing ATL usually experience lymphadenopathy, fever, skin lesions, leucocytosis and hepatosplenomegaly. For indolent ATL subtype (i.e. chronic and smoldering subtypes), the median survival time is approximately 4 years (Takasaki, et al, 2010, *Blood*, 115(22): 4337-4343): 2 to 5 years for the chronic subtype and approximately 3 years for the smoldering one. However, the median survival time for patients with aggressive subtype (i.e. acute, lymphoma, or unfavorable chronic type ATL) decreased to 5 to 13 months even in prospective trials employing multi-agents chemotherapy.

Prognostic factors are advanced performance status, high calcium level, high lactate dehydrogenase level, age (more than 40 years old) and more than three involved lesions. Of note, individuals developing ATL are more prone to develop develop opportunistic infections (Oliere et al, 2011, *Cytokine Growth Factor Rev*, 22(4): 197-210).

Treatment of ATL is dependent on the disease subtype (Oliere et al, 2011, *Cytokine Growth Factor Rev*, 22(4): 197-210). However, therapeutic options are very limited and available therapies only delay the time to relapse.

Although the mechanism of action remains unclear, studies assessing efficacy of the combination of azidothymidine (AZT, Zidovudine) with interferon-alpha gave encouraging results. A meta-analysis of the trials assessing AZT plus interferon-alpha showed that 5-year overall survival reached 46%, a value never reported for any other experimental ATL treatment (Bazarbachi et al, 2010, *J. Clin. Oncol.*, 28(27): 4177-4183). Survival benefit was observed especially in the leukemic ATL subtypes (acute, chronic and smoldering) and when the treatment was administered as first-line. However, treatment with AZT/interferon alpha has many side effects and it is a lifelong treatment without interruption.

Preliminary results of adding arsenic trioxide to this combination therapy suggested that it might be beneficial as consolidation therapy and is worth being investigated further (Kchour, et al, 2013, *Retrovirology*, 10:91).

In Japan, a Phase III clinical trial showed that the mLSG15 regimen that consisted of sequential administration of three drugs associations-VCAP (vincristine, cyclophosphamide, doxorubicin, prednisolone), AMP (doxorubicine, ranimustine, prednisolone) and VECP (vindesine, etoposide, carboplatin, prednisolone)—was superior to biweekly CHOP (cyclophosphamide-hydroxydaunorubicine-oncovin-prednisone) in newly diagnosed acute, lymphoma and unfavourable chronic ATL with median progression-free survival of 7.0 months and overall survival of 12.7 months (Tsukasaki et al, 2007, *J. Clin. Oncol.*, 25(34): 5458-5464).

To date, it is still up to the clinicians to decide whether, depending on the individual benefice risk ratio, to use CHOP or VCAP-AMP-CECP when the treatment option chosen is multiple agents chemotherapy.

During a Phase II clinical trial performed on patients who experienced relapsed or refractory ATL, a humanized monoclonal anti-CC chemokine receptor 4 (CCR4) antibody was shown to be effective for ATL, especially in the acute subtype disease. 27 patients enrolled in the study were treated with the antibody, mogamulizumab. Among the 26 patients who were evaluable, 13 achieved an objective response and among them, 8 a complete response (Ishida et al, 2012, *J. Clin. Oncol.*, 30(8):837-842). In March 2012, mogamulizumab was approved in Japan for the treatment of relapsed or refractory ATL (brand name POTELIOGO®). Post-marketing surveillance reports several serious skin-related adverse events including Stevens-Johnson syndrome (one of them fatal), urging the need to better understand the optimal treatment strategy with mogamulizumab (Ishida et al, 2013, *Cancer Sci.*, 104(5): 647-650). Recently, association of mogamulizumab provided additional progression free survival (PFS) when added to mLSG15 compared to mLSG15 alone, in patients with acute, lymphoma and unfavourable chronic ATL.

Other monoclonal antibodies are being investigated, such as antibody directed against the CD25 which has been assessed in clinical trials, alone or coupled to yttrium-90. An anti-transferrin receptor antibody gave also encouraging results in preclinical stage.

Promising results have been obtained with allogenic hematopoietic stem cell transplantation (allo HSCT) as a curative treatment of ATL. Though, the number of patients who might benefit from this option is very limited (patient developing ATL are usually old and therefore clinicians are reluctant to perform this operation; in addition, finding a compatible donor can prove difficult) (Obama et al, 1999, *Int. J. Hematol.*, 69(3):203-205). Besides, in the few patients eligible for allo HSCT, 30% of patients develop Graft Versus Host disease with severe side effects or leading to death, about 30% of patients relapse and only approximately 30% of patients are cured.

One interesting study reported the successful treatment of a patient with mogamulizumab followed by allo HSCT after treatment failure with chemotherapy (Motohashi et al, 2013, *Int. J. Hematol*, 98(2):258-260).

Hence, although some clinical trials have given encouraging results by increasing the response rates, most of the therapies failed to achieve a significant impact on long-term survival. Moreover, the tested treatments are mainly aggressive ones.

New drugs, already approved or not for treatment of other T-cell lymphomas, are being assessed in ATL patients. These are, for example, the vorinostat and romidepsin histone deacetylase inhibitors (HDAC), FDA-approved for the treatment of relapsed and refractory cutaneous T-cell lymphoma or alemtuzumab, and an anti-CD52 antibody, approved for the treatment of chronic lymphoid leukemia.

New treatments for ATL patients with better overall survival impact, low side effects and possibly not lifelong treatment, either in aggressive or indolent forms of the disease, are desperately searched for.

One hypothesis to explain the long latency period before asymptomatic HTLV-1 carriers (AC) develop ATL is a balance between host immune response and HTLV-1 genome expression (Yoshida, 2010, *Proc. Jpn Acad. Ser. B. Phys. Biol. Sci.*, 86(2): 117-130).

Indeed, several observations and experiments point to a crucial role of host immune system in controlling HTLV-1 spread and the development of HTLV-1 related diseases in infected patients. Among them, in animal model (rat), vertical transmission of HTLV-1 by breastfeeding leads to immunotolerance causing a higher risk for ATL (Hasegawa et al, 2003, *J. Virol.*, 77(5):2956-2963; Komori et al, 2006, *J. Virol.*, 80(15):7375-7381). However, subcutaneous injection of HTLV-1 infected rat cells before oral infection, prevented ATL appearance. Others have reported development of ATL in asymptomatic carriers (AC) treated with immunosuppressants after liver transplant (Kawano et al, 2006, *Transplantation*, 82(6):840-843; Suzuki et al, 2006, *Int. J. Hematol.*, 83(5):429-432). Moreover, an increase of anti-HTLV-1 immune response in ATL patients treated with allo-HSCT has been observed and called Graft Versus Leukemia (GVL) effect, leading to patients' remission (Harashima et al, 2004, *Cancer Res.*, 64(1):391-399). Furthermore, low anti-HTLV-1 immune responses in ATL have been described, which could favor the initiation and progression of the disease in patients (Kannagi et al, 2011, *Cancer Sci.*, 102(4):670-676; Kannagi et al, 2012, *Front. Microbiol.*, 3:323).

In vitro experiments demonstrated that the CTLs specific to HTLV-1 recognized mainly Tax and to a lesser extent, the envelope, polymerase, p12, p30 and HBZ (reviewed in (Kannagi et al, 2012, *Front. Microbiol*, 3:323)). CD8+ T cells originating from AC and ATL patients have been assessed for frequency, diversity and polyfunctionality; results demonstrated an impaired response in these three parameters in ATL versus AC patients (Kozako et al, 2006, *J. Immunol.*, 177(8): 5718-5726; Manuel et al, 2013, *J. Clin. Immunol.*, 33(7):1223-1239).

These, and other studies, demonstrate that specific HTLV-1 cellular immune response is dramatically impaired in patients who have developed ATL. Hence, therapy which aims at stimulate cellular immune response against HTLV-1 infected cells could be an appropriate therapeutic option to treat ATL.

Preclinical studies have already demonstrated the efficiency of a vaccine against the HTLV-1 viral protein Tax in the treatment of ATL phenotype in animal models. Indeed, in a rat model of ATL phenotype (Ohashi et al, 1999, *J. Virol.*, 73(7):6031-6040), in vivo vaccination with Tax DNA induced the stimulation of Tax specific CTLs which are able to lyse HTLV-1 cells in vitro. An adoptive transfer of these CTLs simultaneously with injection of HTLV-1 infected cells inhibits tumor growth in vivo ((Ohashi et al, 2000, *J. Virol.*, 74(20): 9610-9616).

In another study, engraftment of ATL CD4+ cells from acute or chronic ATL subtypes patients leads to ATL like phenotype in NOG mice. Simultaneous injection of CTL from patients, in vitro stimulated with Tax peptides, leads to a decrease in ATL lesions due to an infiltration of CTL in the tumor site, which recognize and kill HTLV-1 tumoral cells Masaki et al, 2013, *J. Immunol.*, 191(1):135-144).

Recently, a clinical trial phase I of a therapeutic vaccine using autologous dendritic cells pulsed with peptides derived from viral protein Tax, as a treatment of ATL, showed preliminary encouraging results: reduction of the proviral load and reduction of the size of the surface lymph nodes (Suehiro, et al, 2013, abstract book from the 16$^{th}$ International Conference on Human Retrovirology: HTLV and Related Viruses). More impressively, 1 of the 2 patients who completed the study achieved a partial remission and the other one has a stable disease without severe side effects.

All these data confirm that the stimulation of the cellular immune response against HTLV-1 cells could be a strong therapeutic option to treat ATL patients.

The first disadvantage of ex vivo peptidic vaccination used in the only clinical trial testing a vaccination against HTLV-1 is the selection of patients eligible for treatment according to their HLA haplotype. Secondly, ex vivo maturation of autologous DCs requires purification steps from PBMCs of patients, leading to repeated depletion of circulated mononuclear cells. In a pathological context, this could be detrimental for the immune system of patients. Moreover, purification of autologous DCs is very expensive and within technical challenge to get good performance (as an example, see PROVENGE® vaccine from Dendreon in prostate cancer treatment (Huber et al, 2012, *J. Natl. Cancer Inst.*, 104(4):273-279)).

Thus, a need exists in the art for improved vectors and methods for treatment of HTLV-1 in humans. The present invention fulfills these needs in the art.

SUMMARY OF THE INVENTION

The invention encompasses compositions comprising lentiviral vectors and uses and methods of using the compositions. The invention encompasses methods, compositions, and uses for inducing an immune response in a human. The lentiviral vector particles can comprise a lentiviral vector, wherein the DNA of the lentiviral vector comprises a promoter directing expression of a polypeptide comprising a HTLV-1 p12p30-Tax-HBZ fusion protein.

In one embodiment, the invention encompasses the use of a composition comprising lentiviral vector particles for induction of an immune response by intramuscular administration to a human, wherein the lentiviral vector particles comprise a lentiviral vector; wherein the DNA of the lentiviral vector comprises a promoter directing expression of a polypeptide comprising a HTLV-1 p12p30-Tax-HBZ fusion protein.

In one embodiment, the invention encompasses a composition comprising lentiviral vector particles for induction of an immune response by intramuscular administration to a human, wherein the lentiviral vector particles comprise a lentiviral vector; wherein the DNA of the lentiviral vector comprises a promoter directing expression of a polypeptide comprising a HTLV-1 p12p30-Tax-HBZ fusion protein.

In some embodiments, the lentiviral vector comprises a β2m promoter or an MHC class I promoter.

In some embodiments, the HTLV-1 p12p30-Tax-HBZ fusion protein is encoded by a DNA having the nucleotide sequence of SEQ ID NO:20.

In some embodiments, the HTLV-1 p12p30-Tax-HBZ fusion protein comprises the amino acid sequence of SEQ ID NO:66.

In some embodiments, the composition comprises at least $10^7$ lentiviral vector particles.

BRIEF DESCRIPTION OF THE DRAWINGS

FIG. 1 depicts T-cell specific immune response (ELISpot IFN-γ) elicited in C57Bl/6j mice after injection of different doses (1.10e6, 1.10e7, 1.10e8 TU/mouse) of lentiviral vectors containing the p12Ip30II HTLV-1 antigen, according to pool of peptides used (p12I or p30II specific) for stimulation of T-cells (cumulative response, median).

DETAILED DESCRIPTION OF THE INVENTION

Figure 2:
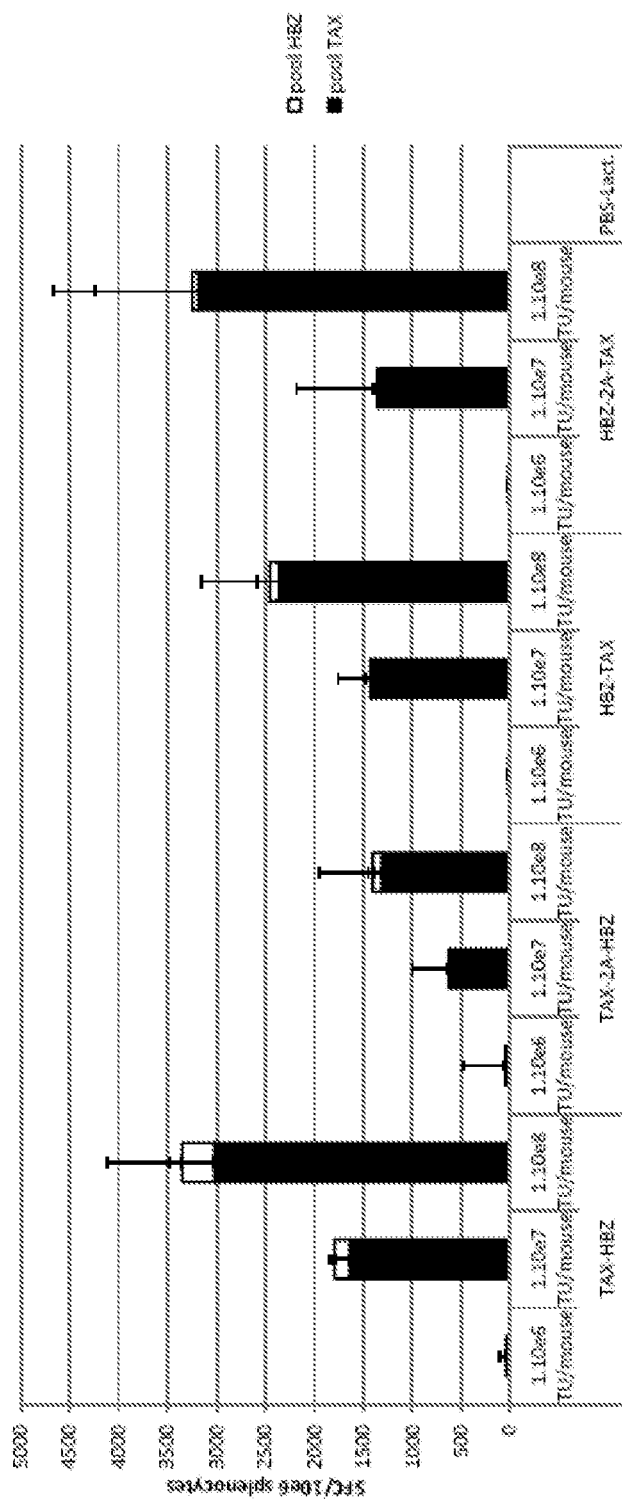
FIG. 2 depicts T-cell specific immune response (ELISpot IFN-γ) elicited in C57Bl/6j mice after injection of different doses (1.10e6, 1.10e7, 1.10e8 TU/mouse) of lentiviral vectors containing different combination of antigens Tax and HBZ, i.e. Tax-HBZ, Tax-2A-HBZ, HBZ-Tax, HBZ-2A-Tax, according to pool of peptides used (Tax or HBZ specific) for stimulation of T-cells (cumulative response, median).

Lentivectors can induce a strong, lasting and diversified T-cell mediated response. Then, cellular immune response against antigen encoded by lentiviral vector is activated. In addition, contrarily for instance to the combination of AZT with interferon-alpha that is a lifelong treatment with severe side effects (i.e. autoimmune disease), efficient therapeutic vaccination could allow the patients to stop taking their treatments for a sustainable period of time, thereby reducing the adverse effects, costs etc.

In contrast to other retroviruses, HTLV-1 displays a remarkable genetic stability; probably due to the viral spread via clonal expansion of infected cells (replication driven by mitosis) rather than through reverse transcription (i.e. de novo infection of previously uninfected cells) which is prone to error. Thus, a lentiviral vector encoding an anti-HTLV-1 antigen could be used to treat patients worldwide.

Four HTLV-1 proteins were chosen to design an anti-HTLV-1 antigen, based on their involvement in host cell regulation mechanisms of proliferation and transformation: Tax, HBZ, p12I and p30II.

Tax Protein

Early steps in the transformation of CD4+ T Lymphocytes by the HTLV-1 have been associated with the oncogenic properties of its main oncogene, Tax. This viral protein is localized in the nucleus of the host cell and interacts with transcription factors or chromatin modellers to promote cell proliferation (Haller et al, 2000, *AIDS Res. Hum. Retroviruses*, 16(16):1683-1688; Jeang, 2001, *Cytokine Growth Factor Rev.*, 12(2-3): 207-217; Azran et al, *Retrovirology*, 1:20 2004; Boxus et al, 2008, *Retrovirology*, 5:76). It has been demonstrated that the expression of Tax leads to a proliferation and differentiation of T lymphocytes through an activation of several cellular signaling pathways (i.e. NF-kB, SRF or AP1). Tax also compromises genome stability by modulating the timing of replication origin activation and the generation of reactive oxygen species leading to DNA double strand breaks. In addition, Tax has been described to display an opposite effect regarding host cell apoptosis. Indeed, at a low level of expression, Tax inhibits cell apoptosis (Brauweiler, et al, 1997, *Virology*, 231(1): 135-140; Tsukahara et al, 1999, *J. Virol.*, 73(10):7981-7987; Kasai and Jeang, 2004, *Retrovirology*, 1:7), and is considered mutagenic and oncogenic (for review see (Boxus, et al, 2008, *Retrovirology*, 5:76)). In contrast, at a high level of expression, Tax seems toxic for cells and induce apoptosis and rapid senescence (Chen et al, 1997, *J. Gen. Virol.*, 78(Pt12):3277-3285; de La Fuente et al, 2000, *J. Virol.*, 74(16):7270-7283; Kao et al., 2000, *Oncogene*, 19(18): 2240-2248; Nicot and Harrod 2000, *Mol. Cell. Biol.*, 20(22): 8580-8589; de la Fuente et al, 2003, *Mol. Cell. Biochem.*, 245(1-2):99-113; Zhang et al, 2009, *Retrovirology*, 6:35; Ho et al, 2012, *J. Virol.*, 86(17):9474-9483). Tax is expressed by the infected cells especially at the early stage of the infection. However, observations have reported that Tax expression is frequently turned off in the acute forms of ATL; at least the dominant circulating clone of HTLV-1 infected cells (Kannagi et al, 2012, *Front. Microbiol.*, 3:323)

HTLV-1 bZIP Factor (HBZ)

The HTLV-1 bZIP factor (HBZ) is another viral protein which is involved in T lymphocytes proliferation. It is encoded by the minus strand of the provirus and is localized in the nucleus of the host cell. It has a bimodal role, HBZ RNA promotes cell proliferation (Satou et al, 2006, *Proc. Natl. Acad. Sci. USA*, 103(3):720-725; Arnold et al, 2008, *Blood*, 112(9):3788-3797z) and HBZ protein might facilitate escape from host immune attack of HTLV-1 infected cells by suppressing the classical NF-κB pathway and by down regulating expression of Tax, the main target of the immune system of infected patients (Gaudray, et al, 2002, *J. Virol.*, 76(24): 12813-12822; Lemasson et al, 2007, *J. Virol.*, 81(4): 1543-1553; Zhao et al, 2009, *Blood*, 113(12):2755-2764). In addition, HBZ has a predominant role in the maintenance of the transformed state and potentially could enable the HTLV-1 to convert T Lymphocytes into Regulatory T Cell, which is thought to be critical for virus persistence.

Accessory Proteins P12I and P30II

P12I is localized in the membrane of Endoplasmic Reticulum (ER) and Golgi apparatus. It is involved in cell proliferation (Nicot et al, 2005, *Oncogene*, 24(39):6026-6034; Edwards et al, 2011, *Viruses*, 3(6): 861-885). Moreover, p12I targets MHCI to degradation and inhibits Natural killer (NK) cell adhesion to cells; preventing HTLV-1 infected cells from being recognized by the immune system (Nicot, et al, 2005, *Oncogene*, 24(39):6026-6034; Banerjee et al, 2007, *J. Virol.*, 81(18):9707-9717). P81 protein, a membrane associated truncated form of p12I, down regulates Tax activity (Fukumoto, et al, 2007, *J. Virol.*, 81(17):9088-9099)).

Finally, p30II is both a nuclear and nucleolar protein which is a negative regulator of viral proteins expression (Nicot, et al, 2004, *Nat. Meth.*, 10(2):197-201; Michael et al, 2006, *Virology*, 354(2): 225-239). P30II contributes to transcriptional and post-transcriptional regulation of several genes involved in cell cycle progression, cell signalling, apoptosis, DNA replication and repair, angiogenesis and cell migration (Taylor et al, 2009, BMC Genomics, 10:311). In addition, p30II interacts with DNA repair pathways Baydoun et al, 2011, *Blood*, 117(22): 5897-5906). Of note, p13II, a spliced isoform of p30II, localized both in mitochondria and in nucleus, is involved in calcium homeostasis and regulation of calcium dependant gene expression, in ROS production and apoptosis (Biasiotto et al, 2010, *Biochim. Biophys. Acta*, 1797(6-7):945-951; Silic-benussi et al, 2010, *Molecular Aspects Med.*, 31(5): 350-358) and in the inhibition of Tax activity (Andresen et al, 2011, *Blood*, 118(6):1549-1559).

Putative Role of Viral Proteins Selected in ATL Pathogenesis

Tax, HBZ, p12I and p30II interact with the cell machinery and disrupt its metabolism. By their action on cell proliferation, on DNA repair and on immune system response, they are considered as oncogenic proteins which can be expressed by leukemic cells despite of the low in vivo expression found in ATL patients (Kannagi, et al, 2012, *Front. Microbiol.*, 3:323). Indeed, Tax is the immunodominant target antigen found in ATL patients (Kannagi et al, 1991, *Int. Immunol.*, 3(8):761-767; Pique et al, 1996, *J. Virol.*, 70(8):4919-4926). In addition, immune response targeting Tax has been observed in ATL patients treated by allo-HSCT who achieved remission (Harashima et al, 2004, *Cancer Res.*, 64(1):391-399). RNA of p12I/p81 is detected in vitro and ex vivo in HTLV-1 infected T cells and macrophages (Koralnik et al, 1992, AIDS Res Hum Retroviruses, 8(11):1845-1849). Moreover, p12I and p30II are targeted in vivo by immune system of HTLV-1 patients, whatever their clinical status (Chen et al, 1997, *Int. J. Cancer*, 71(2):196-202; Dekaban et al, 2000, *Virology*, 274 (1):86-93; Pique and Dokhelar, 2000, *AIDS Res. Hum. Retroviruses*, 16(16):1783-1786). If in vivo HTLV-1 proteins expression is still debated, HBZ expression seems to be conserved in all cases of ATL patients studied (Zhao and Matsuoka, 2012, *Front. Microbiol.*, 3:247). In addition, immune response against HBZ in HTLV-1 carriers has already been observed (Macnamara et al, 2010, *PloS Pathog.*, 6(9):e1001117; Enose-Akahata et al, 2013, *Retrovirology*, 10:19).

Consequently, antigen containing both Tax and HBZ peptidic sequences can be a relevant strategy to stimulate immune response against ATL cells in patients whatever the level of viral proteins expression is, since hypotheses underline the possibility of different pattern of viral protein expression for leukemic cells in patients (Umino et al, 2011, *Blood*, 117(20):5473-5478). Another advantage of Tax and HBZ antigen is the low genetic variability in the sequence (Kubota et al, 2007, *J. Immunol.*, 178(9):5966-5972; Zhao and Matsuoka, 2012, *Front. Microbiol*, 3:247). Finally, p12I and p13II are localized in endomembrane and p81 in lipid rafts of the cell membrane. Owing to membrane trafficking within the cell to the plasma membrane, sequences from these proteins might be present on the cell surface. Choosing epitope in the common sequences of isoform proteins P12I/P81 and P30II/P13II might contribute to an enhanced immune response.

Based on those findings, their expression and the roles of these proteins in the ATL emergence and maintenance, a clinically relevant strategy is to trigger a potent and selective cellular immune response against 1, 2, 3, or all 4 of TAX, HBZ, p12 and p30 antigens.

Design of a Safe Antigen

All the sequences targeting the viral proteins to the subcellular localization where they display their activity were truncated or deleted. In addition, transmembrane domains and sequences involved in interaction with transcriptions factors or other effectors that are not part of major epitopes have been truncated or deleted to abolish any wild type activity. Epitopes from Tax, HBZ, p12I and p30II were combined and fused directly or with linker sequences. Regarding the oncogenic activity of Tax, down regulation of Tax expression by other viral proteins could limit its recognition by the immune system and the lysis of the cell expressing Tax. In the lentiviral vectos, expression of antigen comprising peptides from Tax, HBZ, P12I and P30II, is under control of $\beta 2$ microglobulin promoter, thus antigen is constitutively expressed in host cells and expression cannot be regulated by interaction of viral peptides with $\beta 2$ microglobulin promoter, limiting the risk of oncogenic effect of Tax polypeptide.

In the present study, different combinations of Tax, HBZ, p12I and p30II antigens, have been tested for their capacity to induce a cellular immune response in C57Bl/6j mice.

Figure 1:
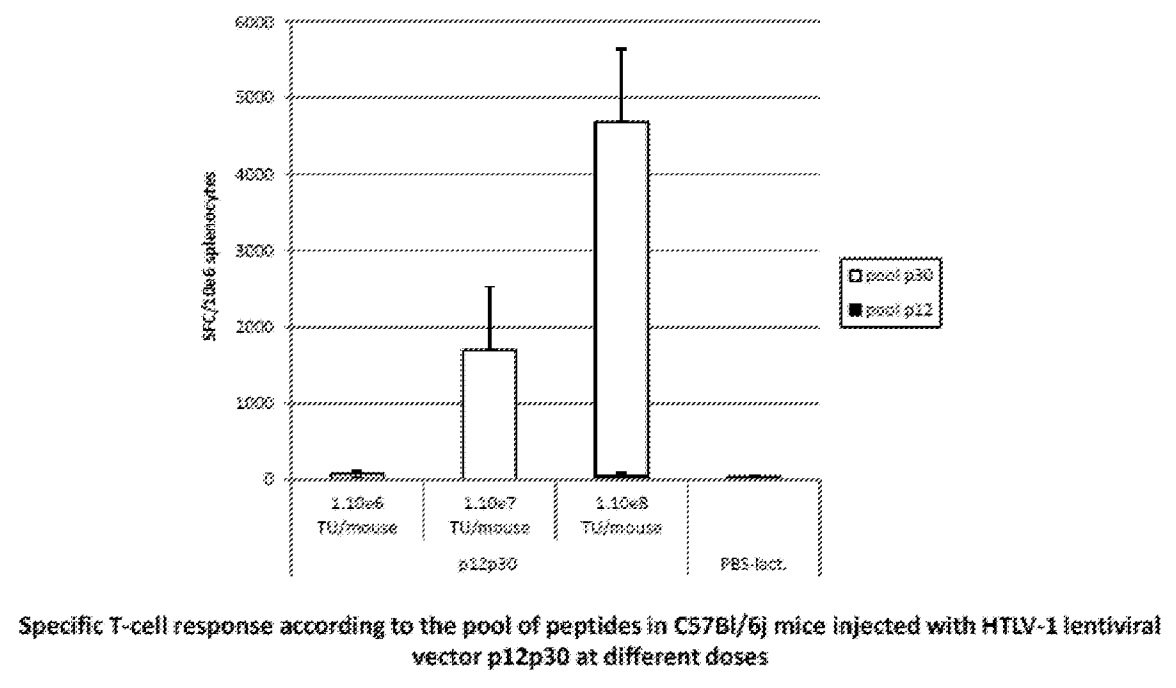
Figure 3:
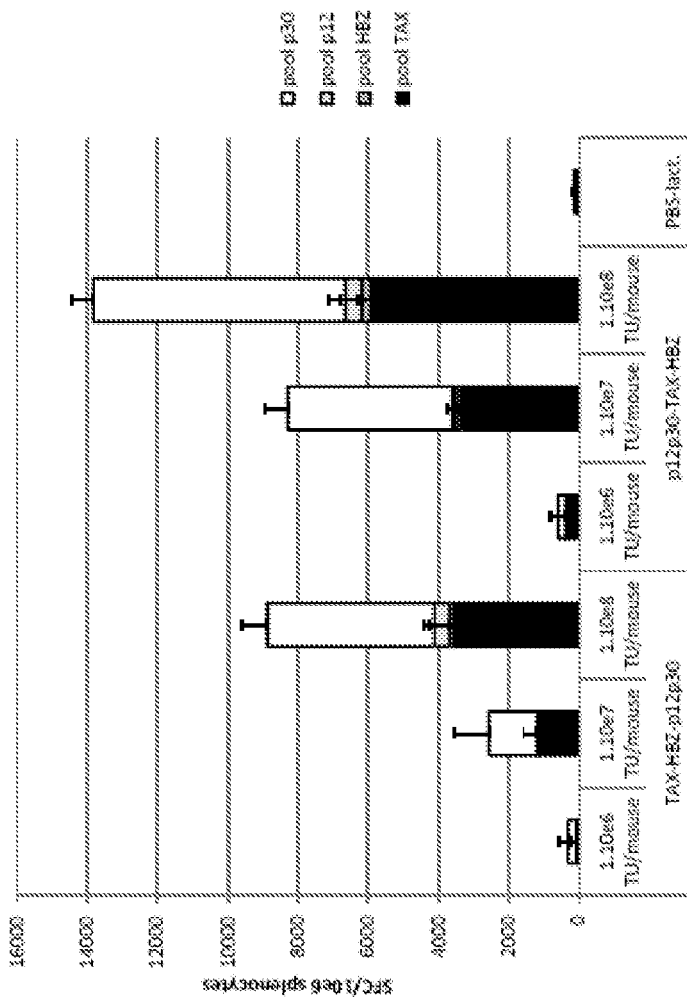
FIG. 3 depicts T-cell specific immune response (ELISpot IFN-γ) elicited in C57Bl/6j mice after injection of different doses (1.10e6, 1.10e7, 1.10e8 TU/mouse) of lentiviral vectors containing different combination of antigens Tax and HBZ, i.e. Tax-HBZ-p12Ip30II and p12Ip30II-Tax-HBZ, according to pool of peptides used (Tax, HBZ, p12I or p30II specific) for stimulation of T-cells (cumulative response).

The T-cell specific response of each combination of HTLV-1 antigens has been evaluated in C57Bl/6j mice by performing Elispot assays (FIGS. 1, 2 and 3). It was demonstrated for the first time that vaccination against HBZ, p12I and p30II can induce a T-cell immune response in animal model.

Surprisingly, T-cell responses varied not only according to antigens (Tax, HBZ, p12I or p30II), but also according to the combination and the construction of these antigens.

For example, FIG. 1 demonstrates that Tax-HBZ antigen induced a stronger T-cell response than HBZ-Tax. In addition, Tax-HBZ antigen seems to be significantly immunogenic at 1.10e6 TU/mouse, contrarily to HBZ-TAX. Interestingly, the construction Tax-2A-HBZ is less immunogenic in C57Bl/6j than Tax-HBZ fused directly without 2A sequence, whereas HBZ-Tax and HBZ-2A-Tax have similar effects.

Tax-HBZ and p12Ip30II antigens were selected to be included together. The Tax-HBZ antigen was fused directly to antigen p12Ip30II in two combinations: p12Ip30II-Tax-HBZ and Tax-HBZ-p12Ip30II. As previously observed, results have demonstrated that T-cell immune response significantly varies according to combination, i.e. p12Ip30II-Tax-HBZ antigen induced a stronger T-cell response in C57Bl/6j mice than Tax-HBZ-p12Ip30II.

The design of an anti-HTLV-1 vaccine has revealed the importance of the combination of the different antigens selected in the induction of a strong and appropriate T-cell immune response in C57Bl/6j mice. The predicted conformation of the polypeptide is as important as the selection of the appropriate epitope in order to develop a vaccine which will have the highest capacity to stimulate a specific immune response. The best antigen combination observed was p12Ip30II-Tax-HBZ antigen.

Figure 4:
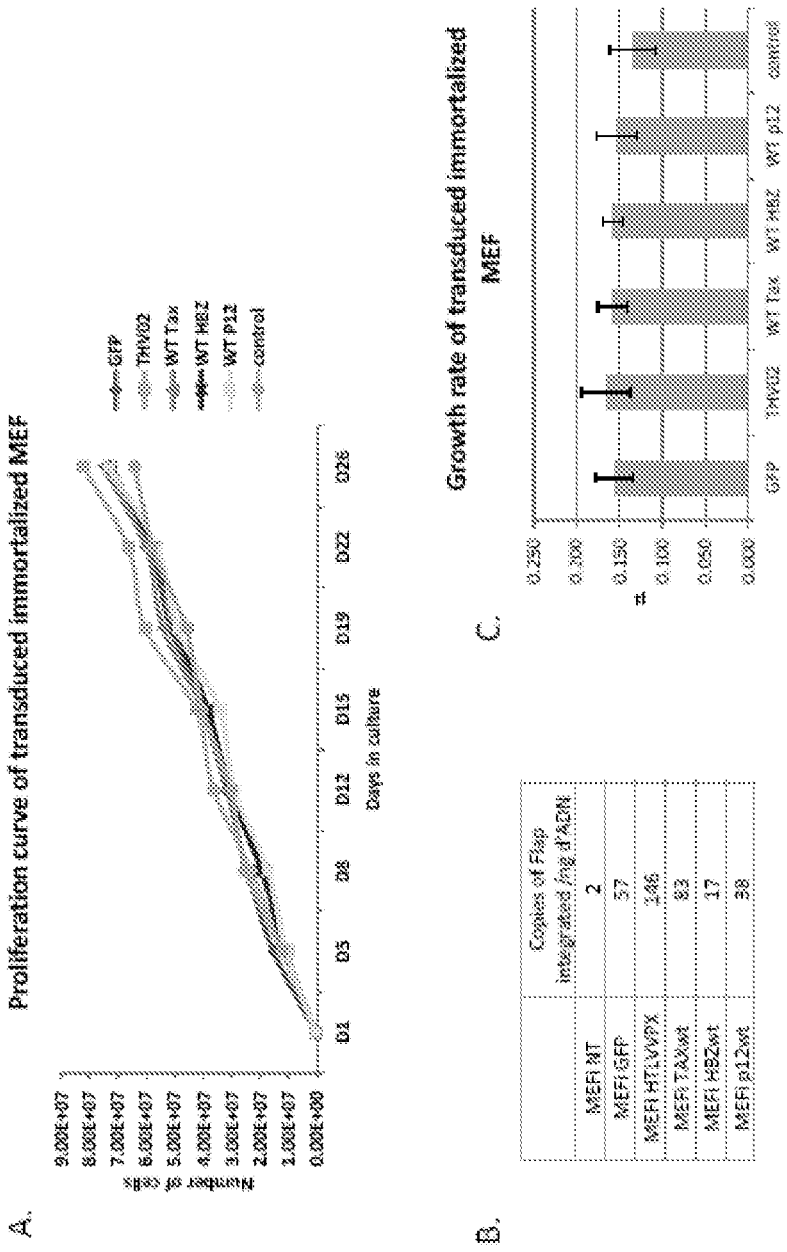
FIG. 4A-C depict lack of effect of lentiviral vectors expressing HTLV antigens in immortalized MEFs in vitro. A. Proliferation curve of transduced immortalized MEFs. B. Copies of integrated vector in MEFs. C. Growth rate of transduced immortalized MEFs.

An in vitro assessment of the carcinogenicity of the lentiviral vector expressing the p12Ip30II-Tax-HBZ antigen was performed. The assessment of safety was performed to assure that antigenic combination does not interfere with cell metabolism after transduction. Primary and immortalized cells (primary and spontaneous immortalized Mouse Embryonic Fibroblast MEF and primary human embryonic fibroblasts MRC5) were transduced with the vector and positive and negative controls. Assessment included growth in inclusion media (agarose), growth during 3 weeks, since cells in 3D don't proliferate/grow unless they present oncogenic properties. Assessment also included microscopic observation of colonies and detection kits. The results are shown in FIG. 4.

Transduction of primary fibroblasts with the lentiviral vector expressing the p12Ip30II-Tax-HBZ antigen resulted in no change of MRC5 morphology. Transduction of immortalized MEF with the lentiviral vector expressing the p12Ip30II-Tax-HBZ antigen resulted in no change of growth during approximately 1 month. No clonogenic cells were found in immortalized MEF transducted with the lentiviral vector expressing the p12Ip30II-Tax-HBZ antigen or even with wt HTLV-1 protein.

Figure 5:
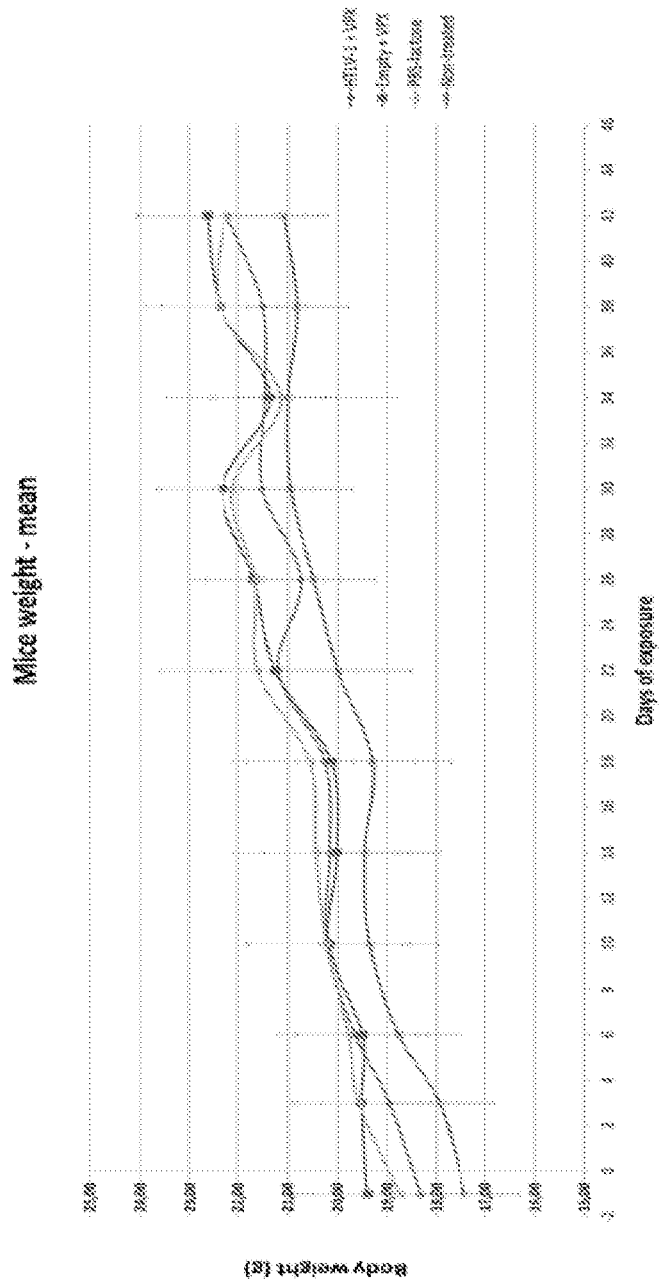
FIG. 5 depicts lack of effect of lentiviral vectors expressing HTLV antigens on mouse weight in vivo.

Carcinogenicity of the lentiviral vector expressing the p12Ip30II-Tax-HBZ antigen+VPX vector in NOG mice was evaluated with negative controls. The results are shown in FIG. 5. No effect on the mice was observed.

Figure 6:
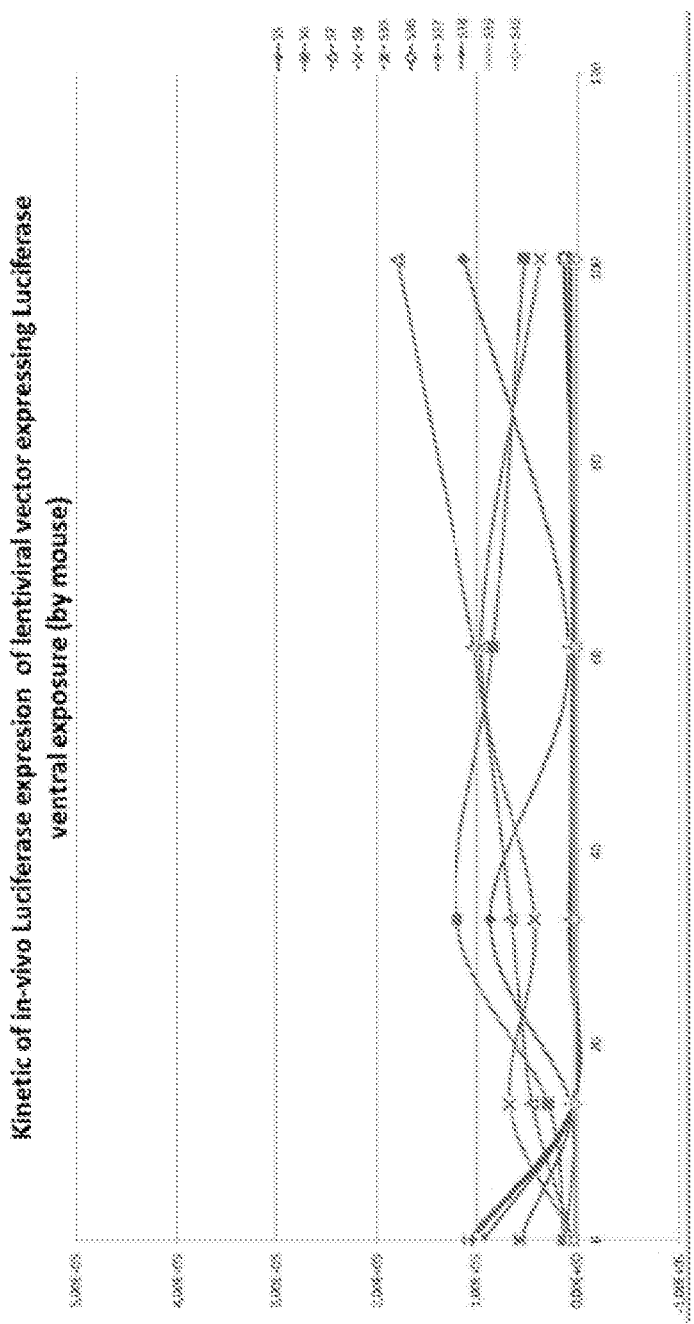
FIG. 6 depicts kinetics of in vivo luciferase expression of transduced mice (ventral exposure). S5-S8 are the lentiviral vector expressing luciferase alone. S35-S38 are the lentiviral vector expressing the p12Ip30II-Tax-HBZ antigen and the luciferase gene (separated from the antigen by a IRES). S39-S40 are non-injected controls.
Figure 7:
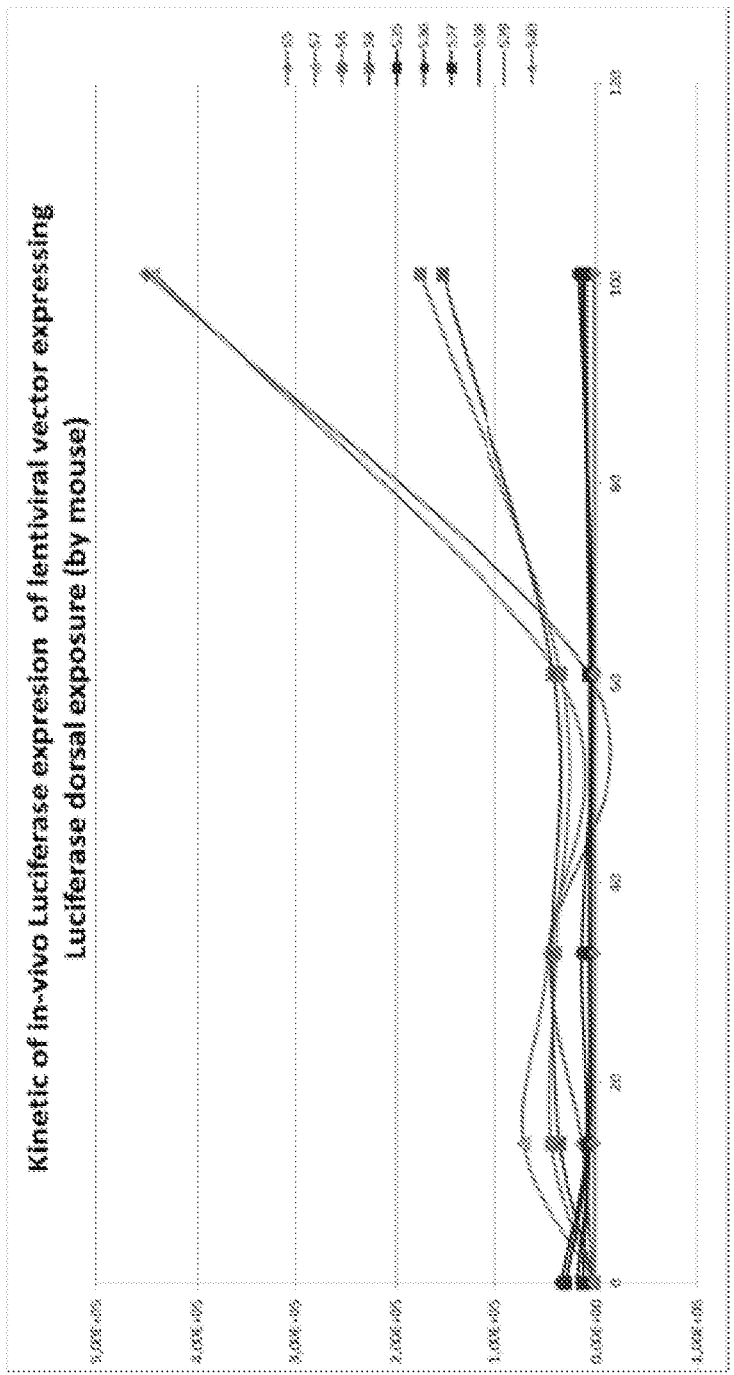
FIG. 7 depicts kinetics of in vivo luciferase expression of transduced mice (dorsal exposure). S5-S8 are luciferase alone. S35-S38 are the lentiviral vector expressing the p12Ip30II-Tax-HBZ antigen and the luciferase gene (separated from the antigen by a IRES). S39-S40 are non-injected controls.

The expression from the lentiviral vector expressing the p12Ip30II-Tax-HBZ antigen in vivo was examined by inserting a luciferase expression cassette into the lentivector, as well as into a control vector. Luciferase expression was monitored by bioluminescence after ventral or dorsal intramuscular injection into NOG mice. The results are shown in FIGS. 6 and 7.

Luciferase expression was seen from 6 hours post administration. In Group 1 (HTLV-Luciferase), bioluminescence was observed to decrease over time. In Group 2 (Luciferase only), bioluminescence was observed to increase over time No tumor growth was observed until the end of the study (Day 66).

The intramuscular administration to an animal of an integrating lentivector with specialized promoters driving expression of an immunogenic protein results in an unexpectedly high and prolonged immune response against the protein that leads to elimination of the integrated vector from the animal. Thus, the invention provides for new lentivectors having high and prolonged immune responses and increased safety for human administration.

Thus, the invention encompasses compositions, methods, and uses employing lentiviral vector particles for induction of an immune response by administration to a human, wherein the lentiviral vector particles comprise a lentiviral vector, wherein the DNA of the lentiviral vector comprises a promoter directing expression of an HTLV-1 Tax and/or HBZ antigen, and/or a p12I and p30II antigen. Preferably, the antigen is encoded by a DNA having the nucleotide sequence of SEQ ID NO:8; SEQ ID NO:10; SEQ ID NO:12; or SEQ ID NO:14-SEQ ID NO:21, Most preferably, the antigen is encoded by SEQ 10 NO:20

MHC Class I and β2m Promoters

The MHC Class I promoters show conservation of NF-Kb binding sites, an interferon stimulated response element (ISRE), and an SXY regulatory module (SXY). The human β2-microglobulin (β2m) promoter shows some similarity to the MHC Class I promoters, as it contains an ISRE, albeit upstream of a single NF-Kb binding site.

MHC Class 11 promoters are considered to be antigen presenting cell (including dendritic cell)-specific promoters. Although MHC class II promoters contain an SXY module, they do not contain NF-Kb binding sites or an ISRE (Van den Helsen et al, 1998, *Immunogenetics*, 48:208-221). Thus, MHC Class 11 promoters are quite different from MHC Class I promoters. As a result, they also have very different cell expression patterns (FIG. 24).

Another antigen presenting cell-specific promoter, dectin-2, contains an interferon stimulated response element (ISRE); but does not contain an SXY module (Bonkabara et al., 2001, J. Immunology, 167:6893-6900).

The sequences of various mammalian (human) MHC class I promoters are shown below:

HLA-A2 (MHC I):
(SEQ ID NO: 1)
attggggagtcccagccttggggattccccaactccgcagtttcttt ctccctctcccaacctatgtagggtccttcttcctggatactcacgac gcggacccagttctcactcccattgggtgtcgggtttccagagaagcc aatcagtgtcgtcgcggtcgcggttctaaagtccgcacgcacccaccg ggactcagattctccccagacgccgagg HLA-B7 (MHC I):
(SEQ ID NO: 2)
ggggaggcgcagcgttggggattccccactcccctgagtttcacttct tctcccaacttgtgtcgggtccttcttccaggatactcgtgacgcgtc cccactcccactcccattgggtattggatatctagagaagccaatca gcgtcgccgcggtcccagttctaaagtcccacgcacccacccggact cagag HLA-Cw5 (MHC I):
(SEQ ID NO: 3)
cactggggaggcgccgcgttgaggattctccactcccctcagtttcac ttcttctcccaacctgcgtcgggtccttcttcctgaatactcatgacg cgtcccaattcccactcccattgggtgtcgggttctagagaagccaa tcagcgtctccgcagtcccggtctaaagtcccagtcacccacccgga ctcagattctccccagacgccgag HLA-E (MHC I):
(SEQ ID NO: 4)
taagaactgctgattgctgggaaactctgcagtttcccgttcctctcg taacctggtcatgtgtccttcttcctggatactcatgacgcagactca gttctcattcccaatgggtgtcgggtttctagagaagccaatcagcgt cgccacgactcccgactataaagtccccatccggactcaagaagttct caggactcagagg HLA-F (MHC I):
(SEQ ID NO: 5)
aggccccgaggcggtgtctggggttggaaggctcagtattgagaattc cccatctcccagagtttctctttctctcccaacccgtgtcaggtcct tcatcctggatactcataacgcggcccatttctcactcccattgggc gtcgcgtttctagagaagccaatcagtgtcgccgcagttcccaggttc taaagtcccacgcaccccgcgggactcatattttcccagacgcggag gttggggtcatg A sequence of the human β2-microglobulin promoter is shown below:
(SEQ ID NO: 6)
aacatcacgagactctaagaaaaggaaactgaaaacgggaaagtccct ctctctaacctggcactgcgtcgctggcttggagacaggtgacggtcc ctgcgggccttgtcctgattggctgggcacgcgtttaatataagtgga ggcgtcgcgctggcgggcattcctgaagctgacagcattcgggccgag.

The MHCI and β2m promoters do not contain an enhancer. Moreover, these promoters are dendritic-specific in that expression of the promoter in BDCA+ dendritic cells is higher than the expression in kidney, smooth muscle, liver, and heart cells. They also have relatively high expression in other transduced cell types, for example, expression of the promoter in BDCA+ dendritic cells is only 12-100 times the expression of that promoter in skeletal muscle cells, in contrast to 900 times with the MHCII HLA-DRa promoter. Id.

The present invention encompasses lentiviral vectors comprising MHCI and β2m promoters, and their use for the induction of immune responses in a host by intramuscular administration.

The present invention encompasses a lentiviral vector comprising a promoter sequence from a class I MHC or β2m gene promoter that directs the transcription of a transgene, which preferably encodes an immunogenic polypeptide, in a cell of a host, preferably in dendritic cells (DCs).

Methods of Administration

The invention encompasses methods of administration of a lentiviral vector (or "lentivector") to a human. Preferably, the lentivector contains a promoter that drives high expression of an antigen in antigen presenting cells, including dendritic cells, and drives expression in other transduced cell types sufficient for elimination by the induced immune response. Most preferably, the promoter lacks an enhancer element to avoid insertional effects.

Preferably, the administration is intramuscular. In one embodiment, the lentivector is injected into the muscle using a needle.

Preferably, the lentivector particle is an integrating lentivector particle, comprising a functional integrase protein.

In one embodiment, the invention comprises a method for inducing an immune response in a human comprising intramuscularly administering lentiviral vector particles. The invention encompasses methods employing lentiviral vector particles for induction of an immune response by intramuscular administration to a human, wherein the lentiviral vector particles comprise a lentiviral vector, wherein the DNA of the lentiviral vector comprises a promoter directing expression of an HTLV-1 Tax and/or HBZ antigen, and/or a p12I and p30II antigen. Preferably, the antigen is encoded by a DNA having the nucleotide sequence of SEQ ID NO:8; SEQ ID NO:10; SEQ ID NO:12; or SEQ ID NO:14-SEQ ID NO:21, most preferably SEQ ID NO:20.

Preferably, the lentivector particles are in a dose of $10^6$, $2\times10^6$, $5\times10^6$, $10^7$, $2\times10^7$, $5\times10^7$, $10^8$, $2\times10^8$, $5\times10^8$, or $10^9$ TU.

The lentivector particles can be administered to the subject in a single dosage, or in multiple (i.e., 2, 3, 4, etc.) dosages. The lentivector particles can be administered in a first (priming) and second (boosting) administration. In one embodiment, the first dosage comprises $10^7$ to $10^8$ TU of lentivector particles and the second dosage comprises $10^7$ to $10^8$ TU of lentivector particles.

The time between the first and second administrations and between an administration and a subsequent administration can vary. In one embodiment, the time between administrations is two to six weeks. In various embodiments, the time between administrations is at least 2, 4, 6, 8, 10, 12, 15, 30, or 52 weeks. In various embodiments, the time between administrations is at least 1, 3, 6, 9, 12, 24, 36, or 48 months. In various embodiments, the time between administrations is at least 1, 2, 3, 4, 5, 6, 7, 8, 9, or 10 years.

Lentiviral Vector

Within the context of this invention, a "lentiviral vector" means a non-replicating vector for the transduction of a host cell with a transgene comprising cis-acting lentiviral RNA or DNA sequences, and requiring lentiviral proteins (e.g., Gag, Pol, and/or Env) that are provided in trans. The lentiviral vector lacks expression of functional Gag, Pol, and Env proteins. The lentiviral vector may be present in the form of an RNA or DNA molecule, depending on the stage of production or development of said retroviral vectors.

The lentiviral vector can be in the form of a recombinant DNA molecule, such as a plasmid. The lentiviral vector can be in the form of a lentiviral particle vector, such as an RNA molecule(s) within a complex of lentiviral and other proteins. Typically, lentiviral particle vectors, which correspond to modified or recombinant lentivirus particles, comprise a genome which is composed of two copies of single-stranded RNA. These RNA sequences can be obtained by transcription from a double-stranded DNA sequence inserted into a host cell genome (proviral vector DNA) or can be obtained from the transient expression of plasmid DNA (plasmid vector DNA) in a transformed host cell.

Preferably the lentiviral vector particles have the capacity for integration. As such, they contain a functional integrase protein. Non-integrating vector particles have one or more mutations that eliminate most or all of the integrating capacity of the lentiviral vector particles. For, example, a non-integrating vector particle can contain mutations in the integrase encoded by the lentiviral pol gene that cause a reduction in integrating capacity. In contrast, an integrating vector particle comprises a functional integrase protein that does not contain any mutations that eliminate most or all of the integrating capacity of the lentiviral vector particles.

Lentiviral vectors derive from lentiviruses, in particular human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV), which are modified to remove genetic determinants involved in pathogenicity and introduce new determinants useful for obtaining therapeutic effects.

Such vectors are based on the separation of the cis- and trans-acting sequences. In order to generate replication-defective vectors, the trans-acting sequences (e.g., gag, pol, tat, rev, and env genes) can be deleted and replaced by an expression cassette encoding a transgene.

Efficient integration and replication in non-dividing cells generally requires the presence of two cis-acting sequences at the center of the lentiviral genome, the central polypurine tract (cPPT) and the central termination sequence (CTS). These lead to the formation of a triple-stranded DNA structure called the central DNA "flap", which acts as a signal for uncoating of the pre-integration complex at the nuclear pore and efficient importation of the expression cassette into the nucleus of non-dividing cells, such as dendritic cells.

In one embodiment, the invention encompasses a lentiviral vector comprising a central polypurine tract and central termination sequence referred to as cPPT/CTS sequence as described, in particular, in the European patent application EP 2 169 073.

Further sequences are usually present in cis, such as the long terminal repeats (LTRs) that are involved in integration of the vector proviral DNA sequence into a host cell genome. Vectors may be obtained by mutating the LTR sequences, for instance, in domain U3 of said LTR (ΔU3) (Miyoshi H et al, 1998, *J Virol.* 72(10):8150-7; Zufferey et al., 1998, *J Virol* 72(12):9873-80).

Preferably, the vector does not contain an enhancer. In one embodiment, the invention encompasses a lentiviral vector comprising LTR sequences, preferably with a mutated U3 region (ΔU3) removing promoter and enhancer sequences in the 3' LTR.

The packaging sequence ψ (psi) can also be incorporated to help the encapsidation of the polynucleotide sequence into the vector particles (Kessler et al., 2007, *Leukemia*, 21(9):1859-74; Paschen et al., 2004, *Cancer Immunol Immunother* 12(6): 196-203).

In one embodiment, the invention encompasses a lentiviral vector comprising a lentiviral packaging sequence ψ (psi).

Further additional functional sequences, such as a transport RNA-binding site or primer binding site (PBS) or a Woodchuck PostTranscriptional Regulatory Element (WPRE), can also be advantageously included in the lentiviral vector polynucleotide sequence of the present invention, to obtain a more stable expression of the transgene in vivo.

In one embodiment, the invention encompasses a lentiviral vector comprising a PBS. In one embodiment, the invention encompasses a lentiviral vector comprising a WPRE and/or an IRES.

Thus, in a preferred embodiment, the lentiviral vector comprises at least one cPPT/CTS sequence, one ψ sequence, one (preferably 2) LTR sequence, and an expression cassette including a transgene, preferably comprising the nucleotide sequence of SEQ ID NO:20, under the transcriptional control of a β2m or class I MHC promoter.

Promoter

In various embodiments, the promoter drives high expression in antigen presenting cells, including dendritic cells, to induce maximal immune responses. Preferably, the promoter drives expression in other transduced cell types sufficient for elimination by the induced immune response. Most preferably, the promoter lacks an enhancer element to avoid insertional effects.

Most preferably, the promoter is not a CMV promoter/enhancer. Preferably, the promoter is not a dectin-2 or MHCII promoter.

In various embodiments, the lentiviral vector comprises a β2m or MHC class I promoter. Preferably, the MHC class I promoter is an HLA-A2 promoter, an HLA-B7 promoter, an HLA-Cw5 promoter, an HLA-F, or an HLA-E promoter. In various embodiments, the promoter sequence comprises a polynucleotide sequence that shares more than 90%, preferably more than 95%, more preferably more than 99% identity with the promoter sequence of SEQ ID NO:1, SEQ ID NO:2, SEQ ID NO:3, SEQ ID NO:4, SEQ ID NO:5, or SEQ ID NO:6.

The invention encompasses lentiviral vectors containing a promoter that does not contain an enhancer.

The invention encompasses the insertion of an MHC Class I (MHCI) or β2 microglobulin (β2m) promoter into a lentiviral vector. As used herein, an "MHC Class I (MHCI) promoter" or "β2 microglobulin promoter" includes a naturally occurring or synthetic MHC Class I promoter or β2 microglobulin promoter. The term "MHC Class I promoter" does not include a β2m promoter.

The promoter can be a naturally occurring promoter. Examples of naturally occurring promoters are the human β2m, HLA-A2, HLA-B7, HLA-Cw5, HLA-E, HLA-F gene promoters. These naturally occurring MHCI promoters are generally cloned or reproduced from the promoter region of a gene encoding the MHC class I protein, or referred to as putatively encoding such proteins in genome databases (ex: NCBI polynucleotide database. Both β2m and class I MHC proteins enter the Major Histocompatibility Complex (MHC).

The proteins encoded by these genes are found in almost all cell types. MHCI proteins are generally present at the surface of the membrane of leucocytes, where they are associated with the β2-microglobulin (β2m). The role of these associated proteins is to present peptides from endogenous sources to CD8+ T cells. They thus play a central role to the generation of the antigen-specific immune response. Because MHC class I proteins have been widely studied and described for many years, their genes are well characterized and detectable using sequence comparison tools, such as the BLAST method (Altschul, S. F. et al. (1990). Basic local alignment search tool. *J. Mol. Biol.* 215(3):403-410).

MHC class I promoters share the ability to be strongly activated in antigen presenting cells, including dendritic cells, as well as, to lower intensity, in the majority of the other human body tissues.

The promoters of the invention can contain further regulatory elements, such as one or more Sp1 and ETs binding sites. In a preferred embodiment, the MHC class I promoter contains 2 Sp1 binding sites and 1 Ets binding site. In other embodiments, Ap1 and/or Ap2 sites are further contained in the promoter.

Preferred promoters are naturally occurring human β2m, HLA-A2, HLA-B7, HLA-Cw5, HLA-E and HLA-F promoters.

Promoters can also be synthetic. Synthetic promoters include promoters that are synthesized using molecular biological techniques to assemble the individual components of a promoter or that are derived from naturally occurring promoters using molecular biological techniques.

In various embodiments, the synthetic promoter comprises a polynucleotide sequence that shares more than 90%, preferably more than 95%, more preferably more than 99% identity, or 100% with the promoter sequence of a 132m or MHC class I gene promoter (e.g., SEQ ID NOs: 1-6).

In one embodiment, the invention encompasses a method comprising inserting a β2m or MHC class I promoter, into a lentiviral vector to direct expression of a transgene, which preferably encodes an HTLV-1 Tax, HTLV-1 bZIP factor (HBZ), and/or an accessory protein P12I and P30II antigen, most preferably comprising or consisting of the amino acid sequence of SEQ ID NO:66. The method can further comprise inserting any of the other nucleic acid elements mentioned herein, such as a DNA flap sequence.

Transgene

Within the context of this invention, a "transgene" is a nucleic acid sequence within a lentiviral vector that is not normally present in a cell to be transduced with the lentiviral vector. The lentiviral vector serves to introduce this sequence into the transduced cell. The term "transgene" does not include those sequences of the vector that facilitate transduction of the transgene. The transgene may be a nucleic acid sequence from another organism. Alternatively, the transgene may be a nucleic acid sequence from the same organism, but having different regulatory sequences controlling its expression. The transgene may be a sense or antisense nucleic acid molecule. According to a preferred embodiment of the invention, the transgene sequence encodes an antigen or immunogenic polypeptide.

Preferably, the antigen or immunogenic polypeptide is a HTLV-1 Tax, HTLV-1 bZIP factor (HBZ), and/or an accessory protein P12I and/or P30II antigen or immunogenic polypeptide. Preferably, several epitopes forming a polyepitope are encoded by the transgene of the invention. In various embodiments, the transgene comprises at least 1, 2, 3, or 4 of the antigens encodes by SEQ ID NO:8; SEQ ID NO:10; SEQ ID NO:12; or SEQ ID NO:14-SEQ ID NO:21.

Preferably, antigen or immunogenic polypeptide comprises or consists of a HTLV-1 p12p30-Tax-HBZ fusion protein.

A particularly preferred HTLV-1 p12p30-Tax-HBZ fusion protein comprises the following amino acid sequence:

```
                                              (SEQ ID NO: 66)
MPKTRRRPRRSQRKRPPTPWQPPPFSLQGLHLAFQLSSIAINPQLLHF

FFPSTMLFRLLSPLSPLALATSAAFFSARLLRRALTMLIISPLPRVWT

EMAHFPGFGQSLLFGYPVYVFGDCVDGRVIGSALQFLIPRLPSFPTQR

TSKTLKVLTPPITHTTPNIPPSFLQAMRKYSPFRNGYMEPTLGQHLPT

LSFPDPGLRPQNLYTLWGGSVVCMYLYQLSPPITWPLLPHVIFCHPGQ

LGAFLTNVPYKRIEKLLYKISLTTGALIILPEDCLPTTLFQPARAPVT

LTAWQNGLLPFHSTLTTPGLIWTFTDGTPMISGPCPKDGQPSLVLQSS

SFIFHKFQTKAYHPSFLLSHGLIQYSSFHNLHLLFEEYTNIPISMLFR

CLPVSCPEDLLVEELVDGLLSLEEELKDKEEEKAVLDGLLSLEEESRG

RLRRGPPGEKAPPRGETHRDRQRRAEEEREKEEEKQIAEYLKRKEEEK

AREKKAADVARRKQEEQER.
```

Both B and T cell-based immune responses can be induced by the same antigen.

Lentiviral Vector Particle Production

The present invention provides a method for producing a lentiviral particle vector, which preferably does not comprise enhancer sequences, but instead contains a β2m or MHCI promoter. A lentiviral particle vector (or lentiviral vector particle) comprises a lentiviral vector in association with viral proteins. The vector is preferably an integrating vector.

Replacing the viral enhancer sequences used in the prior art vectors to drive gene expression with a β2m or MHCI promoter not containing an enhancer can improve the safety of integrating retroviral vectors by:

1) reducing the risk of insertional mutagenesis linked to enhancer sequences; and 2) eliciting an immune response against the product of the transgene such that all the cells where the vector was integrated, whatever the cell-type, are eliminated by the immune system. Thus, after a period of time, the human body may not contain any replicates of such vector.

According to one embodiment of this method, the lentivector particles are obtained in a host cell transformed with a DNA plasmid. Such a DNA plasmid can comprise:

- bacterial origin of replication (ex: pUC ori);
- antibiotic resistance gene (ex: KanR) for selection; and more particularly:
- a lentiviral vector comprising at least one transgene transcriptionally linked to a β2m or MHC class I promoter.

Such a method allows producing a recombinant vector particle according to the invention, comprising the following steps of:

i) transfecting a suitable host cell with a lentiviral vector;

ii) transfecting said host cell with a packaging plasmid vector, containing viral DNA sequences encoding at least structural and polymerase (+ integrase) activities of a retrovirus (preferably lentivirus); Such packaging plasmids are described in the art (Dull et al., 1998, *J Virol,* 72(11):8463-71; Zufferey et al., 1998, *J Virol* 72(12):9873-80).

iii) culturing said transfected host cell in order to obtain expression and packaging of said lentiviral vector into lentiviral vector particles; and iv) harvesting the lentiviral vector particles resulting from the expression and packaging of step iii) in said cultured host cells.

For different reasons, it may be helpful to pseudotype the obtained retroviral particles, i.e. to add or replace specific particle envelope proteins. For instance, this may be advantageous to have different envelope proteins in order to distinguish the recombinant particle from natural particles or from other recombinant particles. In matter of vaccination strategy, pseudotyped particle vectors are more likely to escape the immune system, when this latter already developed immunity against lentiviruses. This is particularly helpful when successive injections of similar particle vectors are required for immunizing a patient against a disease.

In order to pseudotype the retroviral particles of the invention, the host cell can be further transfected with one or several envelope DNA plasmid(s) encoding viral envelope protein(s), preferably a VSV-G envelope protein.

An appropriate host cell is preferably a human cultured cell line as, for example, a HEK cell line.

Alternatively, the method for producing the vector particle is carried out in a host cell, which genome has been stably transformed with one or more of the following components: a lentiviral vector DNA sequence, the packaging genes, and the envelope gene. Such a DNA sequence may be regarded as being similar to a proviral vector according to the invention, comprising an additional promoter to allow the transcription of the vector sequence and improve the particle production rate.

In a preferred embodiment, the host cell is further modified to be able to produce viral particle in a culture medium in a continuous manner, without the entire cells swelling or dying. One may refer to Strang et al., 2005, *J Virol* 79(3):1165-71; Relander et al., 2005, *Mol Ther* 11(3):452-9; Stewart et al., 2009, *Gene Ther,* 16(6):805-14; and Stuart et al., 2011, *Hum gene Ther*., with respect to such techniques for producing viral particles.

An object of the present invention consists of a host cell transformed with a lentiviral particle vector.

The lentiviral particle vectors can comprise the following elements, as previously defined:

- cPPT/CTS polynucleotide sequence; and
- a transgene sequence under control of a β2m or MHCI promoter, and optionally one of the additional elements described above.

Methods for Expressing a Transgene in a Cell

The present invention encompasses methods for expressing a transgene in a cell, preferably a non-dividing cell. The method comprises transducing a cell with a lentiviral vector or lentiviral particle vector of the invention under conditions that allow the expression of the transgene.

The cells are preferably mammalian cells, particularly human cells. Particularly preferred are human non-dividing cells.

The transgene preferably encodes an immunogenic polypeptide. The method can further comprise harvesting or isolating the polypeptide. Particularly preferred polypeptides are those encoded by the nucleotide sequences of SEQ ID NO:8, 10, 12, 14, and 15-21, most preferably SEQ ID NO:20.

The lentiviral vector or lentiviral particle vector preferably comprises a 132m or MHCI promoter.

In one embodiment, the invention encompasses a method for expressing a transgene comprising inserting a transgene of the invention into a lentiviral vector and transducing a cell with the vector containing the transgene.

Therapeutic Use of Lentiviral Vectors

The present invention further relates to the use of the lentiviral vectors according to the invention, especially in the form of lentiviral vector particles, for the preparation of therapeutic compositions or vaccines which are capable of inducing or contributing to the occurrence or improvement of an immunogical reaction against epitopes, more particularly those encoded by the transgene present in the vectors.

The present invention thus provides vectors that are useful as a medicament or vaccine, particularly for intramuscular administration.

These vectors are preferentially used for the treatment or prophylaxis of infectious diseases, especially diseases associated with HTLV-1 virus infection.

As the vectors of the invention more specifically target dendritic cells to obtain a cell-mediated immune response and especially the CTL response associated with the antigen expressed by the transgene in these cells, they are particularly useful as vaccines targeting HTLV-1.

Accordingly, the invention relates to an immunogenic composition comprising a lentiviral vector as previously defined.

The immunogenic compositions of the invention preferably contain cPPT and CTS sequences in the vector and vector particles to induce or to stimulate the nuclear import of the vector genome in the target cells.

During reverse transcription, cPPT and CTS sequences induce the formation of a three stranded DNA structure referred as DNA triplex, which stimulates the nuclear import of DNA vector sequence. Preferably, the vector comprises a transgene and regulatory signals of retrotranscription, expression and encapsidation of retroviral or retroviral-like origin, wherein the composition is capable of inducing or of stimulating a CTL (Cytotoxic T Lymphocytes) and/or a CD4 response against one or several epitopes encoded by the transgene sequence present in the vector.

The expression of the transgene is greatly improved by inclusion of a 82m or MHCI promoter in the vector.

Thus, the lentiviral vectors according to the invention have the ability to induce, improve, or in general be associated with the occurrence of a memory CTL response. In other words, they can be used for the preparation of therapeutic composition for the treatment of HTLV-1-related diseases, by induction of, stimulation of, or participation in the occurrence of a cell-mediated immune response, especially a CTL response or a memory response.

The lentiviral vectors of the invention can be used in methods of treatment and methods of inducing an immune response comprising administering the lentiviral vector to a host and generating a specific immune response against the transgene in the host. The cells and antibodies generated in these hosts can be used as diagnostic reagents.

The lentiviral vectors according to the invention are preferably for intramuscular administration, most preferably by injection with a needle.

In a particular embodiment, the immunogenic composition according to the invention can be directly administered to the patient, in such a way that it will induce, improve, or participate in vivo in the occurrence of a cell-mediated immune response, especially a CTL-mediated immune response.

In another embodiment, the immunogenic compositions are used once or upon repeated administration so that they can enable the occurrence of a long-term memory cell mediated response.

A particular advantage of the immunogenic compositions of the invention is that they can be used to elicit or stimulate a cell-mediated immune response against multiple epitopes encoded by the nucleotides sequence of interest or transgene present in the vector or vector particles.

The invention also encompasses a lentiviral vector comprising a nucleotide sequence encoding a multiple repeat (at least 2 identical sequences) of said amino acid sequence inducing a cellular response and/or an amino acid sequence containing at least 2 different sequences corresponding to 2 epitopes of different antigens. Particularly preferred antigens are those encoded by the nucleotide sequences of SEQ ID NO:8, 10, 12, 14, and 15-21, most preferably SEQ ID NO:20.

As a result, the invention encompasses a composition that could be used in prophylactic and/or therapeutic vaccination protocols, for the treatment of HTLV-1 related diseases.

In particular, it can be used in combination with adjuvants, other immunogenic compositions, chemotherapy, or any other therapeutic treatment.

The invention encompasses a composition for intramuscular administration to a human comprising lentiviral vector particles comprising a functional integrase protein and a lentiviral vector; wherein the DNA of the lentiviral vector comprises a 132m or MHCI promoter directing expression of an antigen. Particularly preferred antigens are those encoded by the nucleotide sequences of SEQ ID NO:8, 10, 12, 14, and 15-21.

The invention encompasses a composition comprising lentiviral vector particles for induction of an immune response by intramuscular administration to a human, wherein the lentiviral vector particles comprise a lentiviral vector, wherein the DNA of the lentiviral vector comprises a promoter directing expression of an HTLV-1 Tax antigen, and wherein the HTLV-1 Tax antigen is encoded by a DNA having the nucleotide sequence of SEQ ID NO:8; SEQ ID NO:15; SEQ ID NO:16; SEQ ID NO:17; SEQ ID NO:18; SEQ ID NO:20; or SEQ ID NO:21.

The invention encompasses a composition comprising lentiviral vector particles for induction of an immune response by intramuscular administration to a human, wherein the lentiviral vector particles comprise a lentiviral vector, wherein the DNA of the lentiviral vector comprises a promoter directing expression of an HTLV-1 HBZ antigen, and wherein the HTLV-1 HBZ antigen is encoded by a DNA having the nucleotide sequence of SEQ ID NO:10; SEQ ID NO:15; SEQ ID NO:16; SEQ ID NO:17; SEQ ID NO:18; SEQ ID NO:20; or SEQ ID NO:21.

The invention encompasses a composition comprising lentiviral vector particles for induction of an immune response by intramuscular administration to a human, wherein the lentiviral vector particles comprise a lentiviral vector, wherein the DNA of the lentiviral vector comprises a promoter directing expression of a P12I antigen (p12I Ag) or P30II antigen (p30II Ag), and wherein the P12I antigen (p12I Ag) or P30II antigen (p30II Ag) antigen is encoded by a DNA having the nucleotide sequence of SEQ ID NO:12; SEQ ID NO:14; SEQ ID NO:19; SEQ ID NO:20; or SEQ ID NO:21.

The invention encompasses the use of a composition comprising lentiviral vector particles for induction of an immune response by intramuscular administration to a human, wherein the lentiviral vector particles comprise a lentiviral vector, wherein the DNA of the lentiviral vector comprises a promoter directing expression of any of the above antigens, and wherein the antigen is encoded by a DNA having the nucleotide sequence of SEQ ID NO:8; SEQ ID NO:10; SEQ ID NO:12; SEQ ID NO:14; SEQ ID NO:15; SEQ ID NO:16; SEQ ID NO:17; SEQ ID NO:18; SEQ ID NO:19; SEQ ID NO:20; or SEQ ID NO:21.

The invention encompasses the use of a composition comprising lentiviral vector particles for induction of an immune response by intramuscular administration to a human, wherein the lentiviral vector particles comprise a lentiviral vector, wherein the DNA of the lentiviral vector comprises a promoter directing expression of a polypeptide comprising a HTLV-1 p12p30-Tax-HBZ fusion protein, preferably wherein the antigen is encoded by a DNA having the nucleotide sequence of SEQ ID NO:20 and/or having the amino acid sequence of SEQ ID NO:66.

Having thus described different embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein.

EXAMPLES

Example 1. Antigens

The following viral proteins have been used to design HTLV-1 antigens for vaccine candidates: Tax, HBZ, p12I and p30II. The corresponding DNA coding sequence and the design of the epitopes are described below.

Tax Sequences

Wild type coding sequence:

(SEQ ID NO: 7)

```
atggcccacttcccagggtttggacagagtcttcttttcggataccca gtctacgtgtttggagactgtgtacaaggcgactggtgccccatctct gggggactatgttcggcccgcctacatcgtcacgccctactggccacc tgtccagagcatcagatcacctgggaccccatcgatggacgcgttatc ggctcagctctacagttccttatccctcgactcccctccttccccacc cagagaacctctaagacccttaaggtccttaccccgccaatcactcat acaacccccaacattccaccctccttcctccaggccatgcgcaaatac tccccettccgaaatggatacatggaacccacccttgggcagcacctc ccaaccctgtcttttccagaccccggactccggccccaaaacctgtac accctctggggaggctccgttgtctgcatgtacctctaccagctttcc ccccccatcacctggcccctcctgccccatgtgatttttgccacccc ggccagctcggggccttcctcaccaatgttccctacaaacgaatagaa aaactcctctataaaatttcccttaccacaggggccctaataattcta cccgaggactgtttgcccaccacccttttccagcctgctagggcaccc gtcacgctgacagcctggcaaaacggcctccttccgttccactcaacc ctcaccactccaggccttatttggacatttaccgatggcacgcctatg atttccgggccctgccctaaagatggccagccatctttagtactacag tcctcctcctttatatttcacaaatttcaaaccaaggcctaccacccc tcatttctactctcacacggcctcatacagtactcttcctttcataat ttgcatctcctatttgaagaatacaccaacatccccatttctctactt
```

-continued

```
tttaacgaaaaagaggcagatgacaatgaccatgagccccaaatatcc cccgggggcttagagcctctcagtgaaaaacatttccgtgaaacagaa gtctga.
```

Main active regions of Tax protein: aa 1-165, nuclear localization sequence; aa 4-174, domain of interaction with Creb 1; aa 67-147, zinc finger domain; aa 217-240, SH3 binding domain; aa 241-285, interaction domain with CrebbP/P300; aa 316-333, interaction domain with lkbkg; aa 337-738, interaction domain with NF-κB; aa 346-435 and aa 637-744, homodimerisation domains; aa 562-606, nuclear export signal; aa 865-966, transactivation domain; aa 934-957, interaction domain with Crebb-Cter; aa 1048-1059, PDZ binding domain.

Tax Antigen (Tax Ag)

(SEQ ID NO: 8)

```
atggcccacttccccggctttggccagagcctgctgttcggctacccc gtgtacgtgttcggcgactgcgtggacggcagagtgatcggcagcgcc ctgcagttcctgatccccagactgcccagcttccccacccagcggacc agcaagaccctgaaggtgctgacccccccatcacccacaccacccccc aatatccccccagcttcctgcaggccatgcggaagtacagccccttc cggaacggctacatggaacccaccctgggccagcatctgcccaccctg agcttccccgatcctggcctgcggccccagaacctgtataccctgtgg ggcggcagcgtcgtgtgcatgtacctgtaccagctgagccctcctatc acctggcccctgctgccccacgtgatcttttgccaccctggacagctg ggcgccttcctgaccaacgtgccctacaagcggatcgagaagctgctg tacaagatcagcctgaccacaggcgccctgatcatcctgcccgaggac tgcctgcccaccaccctgtttcagcccgccagagcccctgtgaccctg accgcctggcagaacggcctgctgcccttccacagcaccctgaccacc cctggcctgatctggaccttcaccgacggcacccccatgatcagcggc ccctgccctaaggacggccagcctagcctggtgctgcagagcagcagc ttcatcttccacaagttccagaccaaggcctaccaccccagctttctg ctgagccacggcctgatccagtactccagcttccacaacctgcatctg ctgttcgaagagtacaccaacatccccatctcc.
```

Nucleotidic sequences which have been removed from Tax Wild Type (WT): aa 73-174; aa 955-1059. Main epitopes found to activate T lymphocytes in ATL patients: aa 31-60; aa 262-288; aa 391-435; aa 451-501; aa 526-585; aa 814-840; aa 901-927 (Kannagi et al, 1992; Arnulf et al, 2004; Suzuki et al, 2012). Active domains truncated or deleted: aa 1-165, nuclear localization sequence; aa 4-174, domain of interaction with Creb 1; aa 67-147, zinc finger domain; aa 865-966, transactivation domain; aa 934-957, interaction domain with Crebb-Cter; aa 1048-1059, PDZ binding domain.

HBZ Sequences

Wild type coding sequence:

(SEQ ID NO: 9)

```
atggcggcctcagggctgtttcgatgcttgcctgtgtcatgcccggag gacctgctggtggaggaattggtggacgggctattatccttggaggaa
```

-continued
gagttaaaggacaaggaggaggagaaagctgtgcttgacggtttgcta tccttagaagaggaaagccgcggccggctgcgacggggccctccaggg gagaaagcgccacctcgcggggaaacgcatcgtgatcggcagcgacgg gctgaggagaagaggaagcgaaaaaaagagcgggagaaagaggaggaa aagcagattgctgagtatttgaaaaggaaggaagaggagaaggcacgg cgcaggaggcgggcggagaagaaggccgctgacgtcgccaggaggaag caggaagagcaggagcgccgtgagcgcaagtggagacaaggggctgag aaggcgaaacagcatagtgctaggaaagaaaaaatgcaggagttgggg attgatggctatactagacagttggaaggcgaggtggagtccttggag gctgaacggaggaagttgctgcaggagaaggaggatttgatgggagag gttaattattggcagggaggctggaggcgatgtggttgcaataa.

Main active regions of HBZ protein: aa 1-24, RNA active domain for transcription activation; aa 259-276, aa 346-360 and aa 412-423, nuclear localization signal; aa 418-576, leucine zipper motif.

HBZ Antigen (HBZ Ag)

(SEQ ID NO: 10)
atgctgttcagatgcctgcccgtgtcctgccccgaggacctgctggtg gaagaactggtggacggcctgctgagcctggaagaggaactgaaggac aaagaggaagagaaggccgtcctggatggcctgctgtctctggaagaa gagagccgggcagactgcggagaggccctcctggcgagaaagccccc cctagaggcgagacacaccgggacagacagagaagggccgaggaagag cgcgagaagaagaggaaaagcagatcgccgagtacctgaagcggaaa gaagaagagaaagcccgcgagaagaaagccgccgacgtggccagacgg aagcaggaagaacaggaacgg.

Nucleotidic sequences which have been removed from HBZ WT: aa 1-24; aa 259-276; aa 346-360; aa 412-627. Main epitopes found to activate T lymphocytes in ATL patients: aa 37-111; aa 133-159; aa 172-198; aa 232-258; aa 310-381; aa 475-621 (MacNamara et al, 2010). Active domains truncated or deleted: aa 1-24, RNA active domain for transcription activation; aa 259-276, aa 346-360 and aa 412-423, nuclear localization signal; aa 418-576, leucine zipper motif.

P12I/p271 Isoform Sequences:
Wild type coding sequence:

(SEQ ID NO: 11)
atgcccaagacccgtcggaggccccgccgatcccaaagaaaaagacct ccaacaccatggcagcctcctccgttcagcctccaaggactccacctc gccttccaactgtctagtatagccatcaatccccaactcctgcatttt ttctttcctagcactatgctgtttcgccttctcagcccttgtctcca cttgcgctcacggcgctcctgctcttcctgcttcctcctagcgacgtc agcggccttcttctccgcccgcctcctgcgccgtgccttctcctcttc cttccttttcaaatactcagcggtctgcttttcctcctctttctcccg ctcttttttcgcttcctcttctcctcagcccgtcgctgccgatcacg atgcgtttccccgcgaggtggcgctttctcccctggagggccccgtcg cagccggccgcggctttcctcttctaa.

Main active regions of p12I/p271 isoform proteins: aa 184-249 and aa 301-360, helical transmembrane domains; aa 235-252 and aa 319-387, leucine zipper; aa 169-183, aa 256-273, aa 367-390 and aa 421-438, SH3 binding domains.

P12I Antigen (p12I Ag)

(SEQ ID NO: 12)
atgcccaagaccagaaggcggcccagaagaagccagagaaagaggccc cctacccctggcagcctcctccattcagtctgcagggcctgcacctg gccttccagctgagcagcattgccatcaaccccagctgctgcacttc ttcttcccttccaccatgctgttccggctgctgagccctctgtctcct ctggccctg.

*Nucleotidic sequences which have been removed from p12I WT: aa 202-456. Main epitopes found to activate T lymphocytes in ATL patients: aa 91-138; aa 169-195; aa 235-279; aa 364-411 and aa 415-456 (Dekaban et al, 2000; Pique et al, 2000). Active domains truncated or deleted: aa 184-249 and aa 301-360, helical transmembrane domains; aa 235-252 and aa 319-387, leucine zipper; aa 256-273, aa 367-390 and aa 421-438, SH3 binding domains.

P30II Sequences
Wild type coding sequence:

(SEQ ID NO: 13)
atggcactatgctgtttcgccttctcagcccttgtctccacttgcgc tcacggcgctcctgctcttcctgcttcctcctagcgacgtcagcggcc ttcttctccgcccgcctcctgcgccgtgccttctcctcttccttcctt ttcaaatactcagcggtctgcttttcctcctctttctcccgctctttt tttcgcttcctcttctcctcagcccgtcgctgccgatcacgatgcgtt tccccgcgaggtggcgctttctcccctggagggccccgtcgcagccgg ccgcggcttcctcttctaaggatagcaaaccgtcaagcacagcttcc tcctcctccttgtcctttaactcttcctccaaggataatagcccgtcc accaattcctccaccagcaggtcctccgggcatgacacaggcaagcat cgaaacagccctgcagatacaaagttaaccatgcttattatcagccca cttcccagggtttggacagagtcttcttttcggatacccagtctacgt gtttggagactgtgtacaaggcgactggtgccccatctctgggggact atgttcggcccgcctacatcgtcacgccctactggccacctgtccaga gcatcagatcacctgggacccccatcgatggacgcgttatcggctcagc tctacagttccttatccctcgactccctccttccccacccagagaac ctctaa.

Main active regions of p30II protein: aa 217-234 and aa 271-294, nuclear localization signal; aa 523-552, mitochondrial targeting signal.

P30II Antigen (p30II Ag)

(SEQ ID NO: 14)
gccaccagcgccgccttttttagcgccagactgctgcggagagccctg accatgctgatcatcagcccctgcccagagtgtggaccgag.

Nucleotidic sequences which have been removed from p30II WT: aa 1-81; aa 127-456; aa 502-723. Main epitopes found to activate T lymphocytes in ATL patients: aa 91-117; aa 466-492; (Pique et al, 2000). Active domains truncated or deleted: aa 217-234 and aa 271-294, nuclear localization signal; aa 523-552, mitochondrial targeting signal.

Example 2. Plasmid Constructions

Different plasmid constructions of the selected antigens have been done, with antigens fused directly or separated by 2A sequence (acg cgt gcc cct gtg aag cag acc ctg aat ttc gat ctg ctg aag ctg gcc ggc gac gtg gag tct aat cct ggc cca act agt) which is a proteolytic sequence that is supposed to help the process of polypeptide (Luke, 2007). The different combinations are: Tax-HBZ, Tax-2A-HBZ, HBZ-Tax, HBZ-2A-Tax, p12Ip30II, Tax-HBZ-p12Ip30II and p12Ip30II-Tax-HBZ, synthetized in optimized codon. The expression of the antigenic combination is under control of the human β2-microglobulin promoter.

Sequences of the different combinations of HTLV-1 antigens tested:

TAX-HBZ (SEQ ID NO: 15)
atggcccacttccccggctttggccagagcctgctgttcggctacccc gtgtacgtgttcggcgactgcgtggacggcagagtgatcggcagcgcc ctgcagttcctgatccccagactgcccagcttccccacccagcggacc agcaagaccctgaaggtgctgacccccccatcacccacaccacccccc aatatccccccagcttcctgcaggccatgcggaagtacagccccttc cggaacggctacatggaacccaccctgggccagcatctgcccaccctg agcttccccgatcctggcctgcggccccagaacctgtataccctgtgg ggcggcagcgtcgtgtgcatgtacctgtaccagctgagccctcctatc acctggcccctgctgccccacgtgatcttttgccaccctggacagctg ggcgccttcctgaccaacgtgccctacaagcggatcgagaagctgctg tacaagatcagcctgaccacaggcgccctgatcatcctgcccgaggac tgcctgcccaccaccctgtttcagcccgccagagcccctgtgaccctg accgcctggcagaacggcctgctgcccttccacagcaccctgaccacc cctggcctgatctggaccttcaccgacggcacccccatgatcagcggc ccctgccctaaggacggccagcctagcctggtgctgcagagcagcagc ttcatcttccacaagttccagaccaaggcctaccaccccagctttctg ctgagccacggcctgatccagtactccagcttccacaacctgcatctg ctgttcgaagagtacaccaacatccccatctccatgctgttcagatgc ctgcccgtgtcctgccccgaggacctgctggtggaagaactggtggac ggcctgctgagcctggaagaggaactgaaggacaaagaggaagagaag gccgtcctggatggcctgctgtctctggaagaagagagccggggcaga -continued ctgcggagaggccctcctggcgagaaagcccccccctagaggcgagaca caccgggacagacagagaagggccgaggaagagcgcgagaaagaagag gaaaagcagatcgccgagtacctgaagcggaaagaagaagagaaagcc cgcgagaagaaagccgccgacgtggccagacggaagcaggaagaacag gaacggtgatga.

HBZ-TAX CO (SEQ ID NO: 16)

atgctgttcagatgcctgcccgtgtcctgccccgaggacctgctggtg gaagaactggtggacggcctgctgagcctggaagaggaactgaaggac aaagaggaagagaaggccgtcctggatggcctgctgtctctggaagaa gagagccggggcagactgcggagaggccctcctggcgagaaagccccc cctagaggcgagacacaccgggacagacagagaagggccgaggaagag cgcgagaaagaagaggaaaagcagatcgccgagtacctgaagcggaaa gaagaagagaaagcccgcgagaagaaagccgccgacgtggccagacgg aagcaggaagaacaggaacggatggcccacttccccggctttggccag agcctgctgttcggctaccccgtgtacgtgttcggcgactgcgtggac ggcagagtgatcggcagcgccctgcagttcctgatccccagactgccc agcttccccacccagcggaccagcaagaccctgaaggtgctgaccccc cccatcacccacaccaccccccaatatccccccagcttcctgcaggcc atgcggaagtacagccccttccggaacggctacatggaacccaccctg ggccagcatctgcccaccctgagcttccccgatcctggcctgcggccc cagaacctgtataccctgtggggcggcagcgtcgtgtgcatgtacctg taccagctgagccctcctatcacctggcccctgctgccccacgtgatc ttttgccaccctggacagctgggcgccttcctgaccaacgtgccctac aagcggatcgagaagctgctgtacaagatcagcctgaccacaggcgcc ctgatcatcctgcccgaggactgcctgcccaccaccctgtttcagccc gccagagcccctgtgaccctgaccgcctggcagaacggcctgctgccc ttccacagcaccctgaccacccctggcctgatctggaccttcaccgac ggcacccccatgatcagcggcccctgccctaaggacggccagcctagc ctggtgctgcagagcagcagcttcatcttccacaagttccagaccaag gcctaccaccccagctttctgctgagccacggcctgatccagtactcc agcttccacaacctgcatctgctgttcgaagagtacaccaacatcccc atctcctgatga.

TAX-2A-HBZ (SEQ ID NO: 17)

atggcccacttccccggctttggccagagcctgctgttcggctacccc gtgtacgtgttcggcgactgcgtggacggcagagtgatcggcagcgcc ctgcagttcctgatccccagactgcccagcttccccacccagcggacc agcaagaccctgaaggtgctgacccccccatcacccacaccacccccc aatatccccccagcttcctgcaggccatgcggaagtacagccccttc cggaacggctacatggaacccaccctgggccagcatctgcccaccctg agcttccccgatcctggcctgcggccccagaacctgtataccctgtgg ggcggcagcgtcgtgtgcatgtacctgtaccagctgagccctcctatc -continued acctggccctgctgccccacgtgatctttgccaccctggacagctg ggcgccttcctgaccaacgtgccctacaagcggatcgagaagctgctg tacaagatcagcctgaccacaggcgccctgatcatcctgcccgaggac tgcctgccaccaccctgtttcagcccgccagagcccctgtgaccctg accgcctggcagaacggcctgctgcccttccacagcaccctgaccacc ctggcctgatctggaccttcaccgacggcacccccatgatcagcggc ccctgccctaaggacggccagcctagcctggtgctgcagagcagcagc ttcatcttccacaagttccagaccaaggcctaccaccccagctttctg ctgagccacggcctgatccagtactccagcttccacaacctgcatctg ctgttcgaagagtacaccaacatccccatctccacgcgtgcccctgtg aagcagaccctgaatttcgatctgctgaagctggccggcgacgtggag tctaatcctggcccaactagtatgctgttcagatgcctgcccgtgtcc tgccccgaggacctgctggtggaagaactggtggacgcctgctgagc ctggaagaggaactgaaggacaaagaggaagagaaggccgtcctggat ggcctgctgtctctggaagaagagagccggggcagactgcggagaggc cctcctggcgagaaagccccccctagaggcgagacacaccgggacaga cagagaagggccgaggaagagcgcgagaaagaagaggaaaagcagatc gccgagtacctgaagcggaaagaagaagagaaagcccgcgagaagaaa gccgccgacgtggccagacggaagcaggaagaacaggaacggtgatga.

HBZ-2A-TAX (SEQ ID NO: 18)

atgctgttcagatgcctgcccgtgtcctgccccgaggacctgctggtg gaagaactggtggacgcctgctgagcctggaagaggaactgaaggac aaagaggaagagaaggccgtcctggatggcctgctgtctctggaagaa gagagccggggcagactgcggagaggccctcctggcgagaaagccccc cctagaggcgagacacaccgggacagacagagaagggccgaggaagag cgcgagaaagaagaggaaaagcagatcgccgagtacctgaagcggaaa gaagaagagaaagcccgcgagaagaaagccgccgacgtggccagacgg aagcaggaagaacaggaacggacgcgtgcccctgtgaagcagaccctg aatttcgatctgctgaagctggccggcgacgtggagtctaatcctggc ccaactagtatggcccacttccccggctttggccagagcctgctgttc ggctaccccgtgtacgtgttcggcgactgcgtggacggcagagtgatc ggcagcgccctgcagttcctgatccccagactgcccagcttccccacc cagcggaccagcaagaccctgaaggtgctgacccccccatcacccac accaccccaatatccccccagcttcctgcaggccatgcggaagtac agccccttccggaacggctacatggaacccacctgggccagcatctg cccaccctgagcttccccgatcctggcctgcggccccagaacctgtat accctgtggggcggcagcgtcgtgtgcatgtacctgtaccagctgagc cctcctatcacctggccctgctgccccacgtgatctttgccaccct ggacagctgggcgccttcctgaccaacgtgccctacaagcggatcgag aagctgctgtacaagatcagcctgaccacaggcgccctgatcatcctg cccgaggactgcctgccaccaccctgtttcagcccgccagagcccct gtgaccctgaccgcctggcagaacggcctgctgcccttccacagcacc ctgaccacccctggcctgatctggaccttcaccgacggcacccccatg atcagcggccctgccctaaggacggccagcctagcctggtgctgcag agcagcagcttcatcttccacaagttccagaccaaggcctaccacccc agctttctgctgagccacggcctgatccagtactccagcttccacaac ctgcatctgctgttcgaagagtacaccaacatccccatctcctgatga.

p12Ip30II (SEQ ID NO: 19)

atgcccaagaccagaaggcggcccagaagaagccagagaaagaggccc cctaccccctggcagcctcctccattcagtctgcagggcctgcacctg gccttccagctgagcagcattgccatcaaccccagctgctgcacttc ttcttcccttccaccatgctgttccggctgctgagccctctgtctcct ctggccctggccaccagcgccgccttttttagcgccagactgctgcgg agagccctgaccatgctgatcatcagccccctgcccagagtgtggacc gag.

p12Ip30II-Tax-HBZ (SEQ ID NO: 20)

atgcccaagaccagaaggcggcccagaagaagccagagaaagaggccc cctaccccctggcagcctcctccattcagtctgcagggcctgcacctg gccttccagctgagcagcattgccatcaaccccagctgctgcacttc ttcttcccttccaccatgctgttccggctgctgagccctctgtctcct ctggccctggccaccagcgccgccttttttagcgccagactgctgcgg agagccctgaccatgctgatcatcagccccctgcccagagtgtggacc gagatggcccacttccccggctttggccagagcctgctgttcggctac cccgtgtacgtgttcggcgactgcgtggacggcagagtgatcggcagc gccctgcagttcctgatccccagactgcccagcttccccacccagcgg accagcaagaccctgaaggtgctgacccccccatcacccacaccacc cccaatatccccccagcttcctgcaggccatgcggaagtacagcccc ttccggaacggctacatggaacccacctgggccagcatctgcccacc ctgagcttccccgatcctggcctgcggccccagaacctgtataccctg tggggcggcagcgtcgtgtgcatgtacctgtaccagctgagccctcct atcacctggccctgctgccccacgtgatctttgccaccctggacag ctgggcgccttcctgaccaacgtgccctacaagcggatcgagaagctg ctgtacaagatcagcctgaccacaggcgccctgatcatcctgcccgag gactgcctgccaccaccctgtttcagcccgccagagcccctgtgacc ctgaccgcctggcagaacggcctgctgcccttccacagcaccctgacc acccctggcctgatctggaccttcaccgacggcacccccatgatcagc ggccctgccctaaggacggccagcctagcctggtgctgcagagcagc agcttcatcttccacaagttccagaccaaggcctaccaccccagcttt ctgctgagccacggcctgatccagtactccagcttccacaacctgcat ctgctgttcgaagagtacaccaacatccccatctccatgctgttcaga tgcctgcccgtgtcctgccccgaggacctgctggtggaagaactggtg -continued gacggcctgctgagcctggaagaggaactgaaggacaaagaggaagag aaggccgtcctggatggcctgctgtctctggaagaagagagccgggc agactgcggagaggccctcctggcgagaaagcccccctagaggcgag acacaccgggacagacagagaagggccgaggaagagcgcgagaagaa gaggaaaagcagatcgccgagtacctgaagcggaagaagaagagaaa gcccgcgagaagaaagccgccgacgtggccagacggaagcaggaagaa caggaacggtgatga.

Tax-HBZ-p12Ip30II
(SEQ ID NO: 21)
atggcccacttccccggctttggccagagcctgctgttcggctacccc gtgtacgtgttcggcgactgcgtggacggcagagtgatcggcagcgcc ctgcagttcctgatcccagactgcccagcttccccacccagcggacc agcaagaccctgaaggtgctgaccccccccatcacccacaccacccc aatatccccccagcttcctgcaggccatgcggaagtacagcccttc cggaacggctacatggaacccaccctgggccagcatctgcccaccctg agcttccccgatcctggcctgcggcccagaacctgtataccctgtgg ggcggcagcgtcgtgtgcatgtacctgtaccagctgagccctcctatc acctggcccctgctgccccacgtgatcttttgccaccctggacagctg ggcgccttcctgaccaacgtgccctacaagcggatcgagaagctgctg tacaagatcagcctgaccacaggcgccctgatcatcctgcccgaggac tgcctgccaccacccctgtttcagcccgccagagcccctgtgaccctg accgcctggcagaacggcctgctgcccttccacagcaccctgaccacc cctggcctgatctggaccttcaccgacggcacccccatgatcagcggc ccctgccctaaggacggccagcctagcctggtgctgcagagcagcagc ttcatcttccacaagttccagaccaaggcctaccacccagctttctg ctgagccacggcctgatccagtactccagcttccacaacctgcatctg ctgttcgaagagtacaccaacatccccatctccatgctgttcagatgc ctgccgtgtcctgccccgaggacctgctggtggaagaactggtggac ggcctgctgagcctggaagaggaactgaaggacaaagaggaagagaag gccgtcctggatggcctgctgtctctggaagaagagagccggggcaga ctgcggagaggccctcctggcgagaaagcccccctagaggcgagaca caccgggacagacagagaagggccgaggaagagcgcgagaagaagag gaaaagcagatcgccgagtacctgaagcggaagaagaagagaaagcc cgcgagaagaaagccgccgacgtggccagacggaagcaggaagaacag gaacggtgatgaatgcccaagaccagaaggcggcccagaagaagccag agaaagaggccccctacccctggcagcctcctccattcagtctgcag ggcctgcacctggccttccagctgagcagcattgccatcaacccccag ctgctgcacttcttcttcccttccaccatgctgttccggctgctgagc cctctgtctcctctggccctggccaccagcgccgccttttttagcgcc agactgctgcggagagccctgaccatgctgatcatcagcccctgccc agagtgtggaccgag.

The antigens are cloned into the pFlap-AG backbone using the BamHI and XhoI restriction sites. pFLAP-AG was generated by amplifying and cloning the proviral region of the pTRIPΔU3-CMV-GFP (Naldini, L. et al. Science. 272, 263-267; 1996) between the SpeI and XbaI sites of the pVAX-1 plasmid (Invitrogen). The resulting plasmid, the pFLAP-CMV-GFP was completed with the SV40 sequence (amplified from the pTRIPΔU3-CMV-GFP and cloned between the PmlI sites), leading to the pFLAP-CMV-GFP-SV plasmid. The CMV promoter was then removed and replaced (between the MluI and BamH1 sites) by the human 32-microglobulin promoter. The resulting plasmide, in which antigen can be cloned in place of the GFP marker (BamH1-XhI sites) was named pFLAP-AG.

Tax_Ag-HBz_Ag, HBz_Ag Tax_Ag, Tax_Ag-HBz_P12I P30II and P12I P30II-Tax_Ag-HBz_Ag. The antigens were obtained separately from GeneArt (Lifetechnologies) and associated together using fusion PCR. Briefly, for each antigenic construction, three separate PCR reactions were performed: the first PCR amplify the first antigen, the second PCR amplify the second antigen, including a 25 bp overhang homologous to the end of the first one. The PCR 1 and 2 products are then gel purified (QIAquick gel extraction kit, QIAGEN) and used as a matrix for the third PCR: products of PCR 1 and 2 hybridized, creating the matrix for the amplification of the whole antigen. Primers used for the three PCR of each construct are shown in table 1. The PCR 3 products were gel purified and cloned in PCR®2.1-TOPO® (Life Technologies), sequenced, digested by BamHI and XhoI restriction enzymes and cloned between the same sites in the pFlap-AG backbone.

Tax_Ag-2A-HBz_Ag and HBz_Ag-Tax_Ag. The antigens were obtained separately from GeneArt (Lifetechnologies) and associated together using PCR. Here, two PCR techniques were used to construct the two antigens. First, two successive elongation PCR were used to add the 50 first nucleotides of the 2A peptide at the end of the first antigen and two successive elongation PCR to add the last 50 nucleotides of the 2A peptide at the beginning of the second antigen. As the two antigens shared 24 nucleotides in common, a fusion PCR were used to reconstruct the final antigen (see above for the description of fusion PCR). Primers used for the PCR are shown in tables 2 and 3. The final PCR product are gel purified and cloned in PCR®2.1-TOPO® (Life Technologies), sequenced, digested by BamHI and XhoI restriction enzymes and cloned between the same sites in the pFlap-AG backbone.

P12I P30II. Codon-optimized P12I P30II was purchase from GeneArt (Lifetechnologies), and was cloned directly in the pFlap-AG using the BamHI and XhoI restriction sites.

Sequences of primers used are shown in Tables 1, 2 and 3.

TABLE 1

Primers used for the three PCR realized to amplify the antigenic constructs.

| | PCR 1: First Antigen (5' to 3') |
|---|---|
| Tax_Ag-HBz_Ag | F1: GGATCCGCCACCATGGCCCACTTTCCA GG (SEQ ID NO: 22) <br> R1: GCTGATAGGGATGTTGGTGTACTCTTC G (SEQ ID NO: 23) |
| HBz_Ag-Tax_Ag | F1: GGATCCGCCACCATGCTGTTCAGATGC CT (SEQ ID NO: 24) <br> R1: GCGTTCCTGTTCTTCCTGCTTCCGTCT G (SEQ ID NO: 26) |

TABLE 1-continued

Primers used for the three PCR realized to amplify the antigenic constructs.

| | |
|---|---|
| Tax_Ag-HBz_Ag-P12IP30II | F1: GGATCCGCCACCATGGCCCACTTTCCAGG (SEQ ID NO: 26)<br>R1: GCGTTCCTGTTCTTCCTGCTTCCGTCTG (SEQ ID NO: 27) |
| P12IP30II-Tax_Ag-HBz_Ag | F1: GGATCCGCCACCATGCCCAAGAGGAGAAG (SEQ ID NO: 28)<br>R1: CTCGGTCCACACTCTGGGCAGGGGCT (SEQ ID NO: 29) |

PCR 2: Second antigen (5' to 3')

| | |
|---|---|
| Tax_Ag-HBz_Ag | F2: AGAGTACACCAACATCCCTATCAGCATGCTGTTCAGATGCCTGCC (SEQ ID NO: 30)<br>R2: CTCGAGTTATCAGCGTTCCTGTTCTTCCTG (SEQ ID NO: 31) |
| HBz_Ag-Tax_Ag | F2: ACGGAAGCAGGAAGAACAGGAACGCATGGCCCACTTTCCAGGCTT (SEQ ID NO: 32)<br>R2: CTCGAGTGATGAGGTGATAGGGATGTTGG (SEQ ID NO: 33) |
| Tax_Ag-HBz_Ag-P12IP30II | F2: GACGGAAGCAGGAAGAACAGGAACGCATGCCCAAGACCAGAAGGCGG (SEQ ID NO: 34)<br>R2: CTCGAGTCATCACTCGGTCCACACTCTGGG (SEQ ID NO: 36) |
| P12IP30II-Tax_Ag-HBz_Ag | F2: CCCCCTGCCCAGAGTGTGGACCGAGATGGCCCACTTTCCAGGCTTTG (SEQ ID NO: 36)<br>R2: CTCGAGTTATCAGCGTTCCTGTTCTTCCTG (SEQ ID NO: 37) |

PCR 3: Whole antigen (5' to 3')

| | |
|---|---|
| Tax_Ag-HBz_Ag | F1: GGATCCGCCACCATGGCCCACTTTCCAGG (SEQ ID NO: 38)<br>R2: CTCGAGTTATCAGCGTTCCTGTTCTTCCTG (SEQ ID NO: 39) |
| HBz_Ag-Tax_Ag | F1: GGATCCGCCACCATGCTGTTCAGATGCCT (SEQ ID NO: 40)<br>R2: CTCGAGTCATCAGCTGATAGGGATGTTGG (SEQ ID NO: 41) |
| Tax_Ag-HBz_Ag-P12IP30II | F1: GGATCCGCCACCATGGCCCACTTTCCAGG (SEQ ID NO: 42)<br>R2: CTCGAGTCATCACTCGGTCCACACTCTGGG (SEQ ID NO: 43) |
| P12IP30II-Tax_Ag-HBz_Ag | F1: GGATCCGCCACCATGCCCAAGAGGAGAAG (SEQ ID NO: 44)<br>R2: CTCGAGTTATCAGCGTTCCTGTTCTTCCTG (SEQ ID NO: 46) |

Sequences in bold represent the 5' overhang homologous to the end of the first antigen.

TABLE 2

Primers used for the successive elongation PCR.

| Primary antigens | | Elongation PCR no 1 (5' to 3') |
|---|---|---|
| Tax_Ag-2A-HBz_Ag | Tax_Ag + 50 nt from 2A | F1: GGATCCGCCACCATGGCCCACTTTCCAGG (SEQ ID NO: 46) |
| | | R1: ATTCAGGGTCTGCTTCACAGGGGCACGCGTGCTGATAGGGATGTTGGTGTACTCTTCGA (SEQ ID NO: 47) |
| | HBz_Ag + 50 nt from 2A | F3: GACGTGGAGTCTAATCCTGGCCCAACTAGTATGCTGTTCAGATGCCTGCCCGTGT (SEQ ID NO: 48) |
| | | R3: CTCGAGTTATCAGCGTTCCTGTTCTTCCTG (SEQ ID NO: 49) |
| HBz_Ag-2A-Tax_Ag | HBz_Ag + 50 nt from 2A | F1: GGATCCGCCACCATGCTGTTCAGATGCCT (SEQ ID NO: 50) |
| | | R1: ATTCAGGGTCTGCTTCACAGGGGCACGCGTGCGTTCCTGTTCTTCCTGCTTCCGTCTG (SEQ ID NO: 51) |
| | Tax_Ag + 50 nt from 2A | F3: GACGTGGAGTCTAATCCTGGCCCAACTAGTATGGCCCACTTTCCAGGCTTTGGCC (SEQ ID NO: 52) |
| | | R3: CTCGAGTCATCAGCTGATAGGGATGTTGG (SEQ ID NO: 53) |
| | | Elongation PCR no 2 (5' to 3') |
| Tax_Ag-2A-HBz_Ag | Tax_Ag + 50 nt from 2A | F1: GGATCCGCCACCATGGCCCACTTTCCAGG (SEQ ID NO: 54) |
| | | R2: GCCGGCCAGCTTCAGCAGATCGAAATTCAGGGTCTGCTTCACAGGGGCAC (SEQ ID NO: 55) |
| | HBz_Ag + 50 nt from 2A | F4: TTCGATCTGCTGAAGCTGGCCGGCGACGTGGAGTCTAATCCTGGCCCAAC (SEQ ID NO: 56) |
| | | R3: CTCGAGTTATCAGCGTTCCTGTTCTTCCTG (SEQ ID NO: 57) |
| HBz_Ag-2A-Tax_Ag | HBz_Ag + 50 nt from 2A | F1: GGATCCGCCACCATGCTGTTCAGATGCCT (SEQ ID NO: 58) |
| | | R2: GCCGGCCAGCTTCAGCAGATCGAAATTCAGGGTCTGCTTCACAGGGGCAC (SEQ ID NO: 59) |

TABLE 2-continued

Primers used for the successive elongation PCR.

| Primary antigens | | |
|---|---|---|
| Tax_Ag + 50 nt from 2A | F4: | TTCGATCTGCT GAAGCTGGCCGGCGA CGTGGAGTCTAATCC TGGCCCAAC (SEQ ID NO: 60) |
| | R3: | CTCGAGTCATC AGCTGATAGGGATGT TGG (SEQ ID NO: 61) |

TABLE 3

Primers used for the fusions PCR realized to amplify the whole antigenic constructs.

| | Fusion PCR: whole antigens (5' to 3') |
|---|---|
| Tax_Ag-2A-HBz_Ag | F1:GGATCCGCCACCATGGCCCACT TTCCAGG (SEQ ID NO: 62) R3:CTCGAGTTATCAGCGTTCCTGT TCTTCCTG (SEQ ID NO: 63) |
| HBz_Ag-2A-Tax_Ag | F1:GGATCCGCCACCATGCTGTTCA GATGCCT (SEQ ID NO: 64) R3:CTCGAGTCATCAGCTGATAGGG ATGTTGG (SEQ ID NO: 65) |

Example 3. Lentiviral Vector Production

The lentivectors were packaged by cotransfection in HEK 293 T cells with the plasmid containing the HTLV-1 antigen to be tested, an encapsidation plasmid, a plasmid providing VSV.G envelope, essentially as described in Naldini et al, 1996, Science 272:263-7.

Example 4. Immunomonitoring

To monitor the specific T-cell responses for each combination of HTLV-1 antigens, C57Bl/6j mice were immunized intramuscularly with $1 \times 10^6$ TU, $1 \times 10^7$ TU and $1 \times 10^8$ TU of lentivectors in which HTLV-1 antigens expression is driven by the human β2-microglobulin promoter. 14 days after immunization, splenocytes were isolated from the mice spleens immunized with lentivectors and were used for the ELISPOT assays. Ninety-six-well tissue culture plates (Millipore) were coated overnight at 4° C. with 100 µl/well of 5 µg/ml anti-mouse IFNγ mAb (Mouse IFNγ Elispot pair; BD Biosciences Pharmingen). The plates were washed three times with 200 µl DPBS/well and blocked with 200 µl/well of RPMI media/10% fetal bovine serum for 2 h at 37° C. The plates were washed three times with 200 µl DPBS/well. Splenocytes were added to the plates in triplicate at $1 \times 10^5$ cells/well and stimulated with 2 µg/ml of stimulatory pools of peptides (specific to the antigen), concanavalin A (5 µg/ml; source), or culture medium alone. The plates were incubated for 18 h at 37° C. and then rinsed three times with 200 µl/well of DPBS/0.05% TWEEN™ 20 and three times with 200 µl of DPBS. For detection, 10 µl/well of 2 µg/ml anti-mouse IFNγ-biotinylated monoclonal antibody (BD Pharmingen) were added for 2 h at room temperature. Plates were washed and 100 µl/well of streptavidin-alkaline phosphatase (Roche) diluted 1:2000 in Dulbecco's PBS for 90 min at room temperature. After washing the plates, spots (IFNγ-secreting cells) were visualized by adding 100 µl/well of BCIP/NBT solution (Sigma). Plates were incubated for 15-30 min at room temperature until blue spots developed and then thoroughly washed with running tap water and air-dried for 24 h. Spots were counted using an AID reader (Autoimmun Diagnostika GmbH, Germany). Mean number of IFNg spots-forming-cells (SFC) per million was calculated from triplicate wells after subtracting the one from control wells (cultured in medium without peptides). Overlapping synthetic peptides covering HTLV-1 complete sequence used for vaccination were used (Genscript)

Example 5. In Vitro Oncogenicity Studies

Cell Culture

Mouse Embryonic fibroblast (MEF; ATCC reference SCRC-1008) were immortalized spontaneously (MEFi) after 10 serial passages. They were cultured in Dubbelco's modified Eagle's medium (DMEM) supplemented with 10% heat inactivated FBS (Hyclone, New Zealand), 2 mM Glutamine (Life, France), 100 Units/mL penicillin-streptomycin (Life, France), 1 mM Sodium-Pyruvate (Life, France) in a humidified atmosphere of 5% CO2 at 37° C.

Transduction 100 000 cells per well were plated in 6-well plates (Multiwell TC plates, Falcon, France) and allowed to adhere during 4 hours at 37° C., 5% CO2 and humidified atmosphere. Then, they were transduced twice: Initially for 2 hours and then for 16 hours with an MOI of 10 lentiviral GFP, THVO2, WT TAX, WT HBZ or WT p12 vectors supplemented with 4 µg/mL Hexadimethrine bromide (Sigma, France). Culture medium was removed the following day to allow the transduced cells to grow in a lentivector free-medium for 2 days. Pictures of the control GFP transduced cells were taken using a green fluorescent light microscope (Olympus CKX41) to valid the transduction efficacy.

Colony Formation Assay

MEFi and transduced MEFi cells were trypsinized after 3 days in lentivector-free medium culture with trypLE Select (Life, France), counted and included in 0.4% soft agar supplemented with complete medium (Life, France) in 24-well white plates (Berthold, France) coated with 0.8% agarose (Life, France). To generate the reference curve, 0 to 32 000 non-transduced MEFi cells were plated; while 8000 cells of transduced MEFi were plated. Cells were grown for 21 days and potential colonies formation was monitored. All experiments were performed in duplicate with two independent experiments.

Microscopic Evaluation of Colonies

All plate wells were examined under bright-field conditions with an Olympus CKX41 microscope and documented using a 10×/0.25 lens and a XC30 camera AnalySIS getIT software. A colony was defined as being >10 counted cells.

The cells viability was observed with the Cyquant direct cell proliferation assay (see below) under a fluorescent light using an Olympus CKX41 microscope.

Cell Proliferation Assays

The Cyquant direct cell proliferation assay (Life, France) was performed according to the manufacturer's recommendations and analyzed using the AnalySIS getIT software by counting viable cells and viable clonogenic cells.

Cell Titer Glo ATP bioluminescence assay (Promega, France) was performed according to the manufacturer's instructions with the exception of the incubation period duration (1 hour at 37° C.) for a better lysis of included cells. Analysis was performed using a Tristar2 multimode reader (Berthold, France). The assay was considered valid when the bioluminescent intensity of the range was linear from 0 to at least 16 000 cells.

An amplification curve was done by counting cells every 4 to 5 days during one month. Cells were trypsinized with TrypLE select (Life, France) and counted on Nuclecounter cassette (Sartorius, France). Then, they were seeded at 500 000 cells on TC flasks T162 (Corning, France) and cultured in a humidified atmosphere at 37° C. and 5% CO2.

DNA Extraction and qPCR

After 4 days of transduction, 1 to $2.10^{-6}$ cells were trypsinized and pelleted by centrifugation at 450 g and extracted with a Qiagen DNA extraction mini kit (Qiagen, France) according to the manufacturer's protocol.

A qPCR was used to determine the number of integrated copy of flap perng of DNA. qPCR was done according to internal procedures in CFX-96 (Bio-Rad, France) with flap primers and specific FAM probe. Sequences used were: TGG AGG AGG AGA TAT GAG GG (Fw)(SEQ ID NO:67), CTG CTG CAC TAT ACC AGA CA (Rv) (SEQ ID NO:68), and FAM-AACCATTAGGAGTAGCACCCACCAAGG-BBQ2 (probe) (SEQ ID NO:69).

The concentration of DNA was measured with a Nano-drop (ThermoScientific, France).

RNA Extraction and qRT-PCR

Total RNA was extracted from MEFi and MEFi THVO2 transduced cell using the NucleoSpin RNA Extraction (Macherey Nagel, France) before being reverse transcribed with the SuperScript II Reverse Transcriptase (Life, France) and amplified by SsoAdvanced SYBR Green Supermix (Bio-Rad, France) according to the CFX-96 (Bio-Rad, France) manufacturer's instructions. The primer sequences used to detect THVO2 were TCATCTTCCACAAGTTCCAGAC (Forward) (SEQ ID NO:70) and GATAGGGATGTTGGT-GTACTCTTC (Reverse) (SEQ ID NO:71). Amplification products were visualized in real-time on Bio-Rad CFX-Manager software.

Example 6. In Vivo Carcinogenicity Studies

CIEA NOG immunodeficient mice were purchased from TACONIC. Upon receipt, the animals were separated, caged in groups of five animals and acclimated for 1 week. After acclimation, the animals were distributed randomly to test groups. All animals were 7 weeks of age at the initiation of the studies. The study consisted of a control group (non-treated mice) and three treatment groups (HTLV-1.VPX vector, Empty.VPX vector and placebo group—PBS-lactose). Each group contained 7 mice and the animals were observed during 3 months. The lentiviral vectors and the placebo were administrated intramuscularly with the maximal achievable dose of studied vectors, respectively: $2.08 \times 10^7$ TU/mouse of HTLV-1.VPX vector and $3.53 \times 10^8$ TU/mouse of Empty.VPX vector. All test animals were observed each week fot general physical condition and behavior and the observations were recorded. Detailed physical examinations were conducted on each animal at weekly intervals to evaluate for abnormal changes in such parameters as condition of pelage, muscle tone, respiration, locomotion and posture. The animals were examined for the presence of external palpable tumors. Body weights and food consumption were assessed. At the end of the study animals were necropsied and tissues were fixed for subsequent histopathological evaluation.

Example 7. In Vivo Bioluminescence/Expression Studies

CIEA NOG immunodeficient mice were purchased from TACONIC. Upon receipt, the animals were separated, caged in groups of four or five animals and acclimated for 2 weeks. After acclimation, the animals were distributed randomly to test groups. All animals were 5 weeks of age at the initiation of the studies. The study consisted of a control group (non-treated mice) and two treatment groups (HTLV-1.Luciferase vector, Luciferase vector). Each group contained 19 mice (treated animals) and 17 mice—non-treated group. The animals were observed during 3 months. The lentiviral vectors were administrated intramuscularly with the maximal achievable dose of studied vectors, respectively: $2.98 \times 10^8$ TU/mouse of HTLV-1.Luciferase vector and $5.56 \times 10^7$ TU/mouse of Luciferase vector. All test animals were observed each week for general physical condition and behavior and the observations were recorded. Detailed physical examinations were conducted on each animal at weekly intervals to evaluate for abnormal changes in such parameters as condition of pelage, muscle tone, respiration, locomotion and posture. The animals were examined for the presence of external palpable tumors. Body weights and food consumption were assessed. At the end of the study animals were necropsied and tissues were fixed for subsequent histopathological evaluation.

Imaging and quantification of bioluminescence in vivo: Measurements were performed with an ultrasensitive cooled CDD camera mounted with in a light-tight camera box (IVIS Spectrum, Xenogen). Images and measurements of bioluminescent signals were acquired and analyzed using Living image software 2.5 (Xenogen). To image, mice were anesthetized by isoflurane inhalation and given 200 μL of 15 mg/mL D-luciferin (Caliper Lifesciences) via intraperitoneal injection. Images were taken 1 minute after D-luciferin injection.

We claim:

1. A method for inducing an immune response comprising intramuscularly administering to a human a composition comprising lentiviral vector particles, wherein the lentiviral vector particles comprise a lentiviral vector;

wherein DNA of the lentiviral vector comprises a promoter directing expression of a polypeptide comprising a HTLV-1 p12p30-Tax-HBZ fusion protein.

2. The method of claim 1, wherein the lentiviral vector comprises a β2m promoter.

3. The method of claim 1, wherein the lentiviral vector comprises an MHC class I promoter.

4. The method of claim 1, wherein the HTLV-1 p12p30-Tax-HBZ fusion protein is encoded by a DNA having the nucleotide sequence of SEQ ID NO:20.

5. The method of claim 1, wherein the HTLV-1 p12p30-Tax-HBZ fusion protein comprises the amino acid sequence of SEQ ID NO:66.

6. The method of claim 1, comprising at least $10^7$ lentiviral vector particles.

7. A composition comprising lentiviral vector particles for induction of an immune response by intramuscular administration to a human, wherein the lentiviral vector particles comprise a lentiviral vector;

wherein the DNA of the lentiviral vector comprises a promoter directing expression of a polypeptide comprising a HTLV-1 p12p30-Tax-HBZ fusion protein.

8. The composition of claim 7, wherein the lentiviral vector comprises a β2m promoter.

9. The composition of claim 7, wherein the lentiviral vector comprises an MHC class I promoter.

10. The composition of claim 7, wherein the HTLV-1 p12p30-Tax-HBZ fusion protein is encoded by a DNA having the nucleotide sequence of SEQ ID NO:20.

11. The composition of claim 7, wherein the HTLV-1 p12p30-Tax-HBZ fusion protein comprises the amino acid sequence of SEQ ID NO:66.

12. The composition of claim 7, comprising at least $10^7$ lentiviral vector particles.

* * * * *

SEQUENCE LISTING

```
<160> NUMBER OF SEQ ID NOS: 71

<210> SEQ ID NO 1
<211> LENGTH: 220
<212> TYPE: DNA
<213> ORGANISM: Homo sapiens

<400> SEQUENCE: 1
attggggagt cccagccttg gggattcccc aactccgcag tttcttttct ccctctccca      60
acctatgtag ggtccttctt cctggatact cacgacgcgg acccagttct cactcccatt     120
gggtgtcggg tttccagaga agccaatcag tgtcgtcgcg gtcgcggttc taaagtccgc    180
```

```
acgcacccac cgggactcag attctcccca gacgccgagg                              220
```

<210> SEQ ID NO 2
<211> LENGTH: 197
<212> TYPE: DNA
<213> ORGANISM: Homo sapiens

<400> SEQUENCE: 2

```
ggggaggcgc agcgttgggg attccccact cccctgagtt tcacttcttc tcccaacttg       60
tgtcgggtcc ttcttccagg atactcgtga cgcgtcccca cttcccactc ccattgggta      120
ttggatatct agagaagcca atcagcgtcg ccgcggtccc agttctaaag tccccacgca      180
cccacccgga ctcagag                                                     197
```

<210> SEQ ID NO 3
<211> LENGTH: 216
<212> TYPE: DNA
<213> ORGANISM: Homo sapiens

<400> SEQUENCE: 3

```
cactggggag gcgccgcgtt gaggattctc cactcccctc agtttcactt cttctcccaa       60
cctgcgtcgg gtccttcttc ctgaatactc atgacgcgtc cccaattccc actcccattg      120
ggtgtcgggt tctagagaag ccaatcagcg tctccgcagt cccggtctaa agtccccagt      180
cacccacccg gactcagatt ctccccagac gccgag                                216
```

<210> SEQ ID NO 4
<211> LENGTH: 205
<212> TYPE: DNA
<213> ORGANISM: Homo sapiens

<400> SEQUENCE: 4

```
taagaactgc tgattgctgg gaaactctgc agtttcccgt tcctctcgta acctggtcat       60
gtgtccttct tcctggatac tcatgacgca gactcagttc tcattcccaa tgggtgtcgg      120
gtttctagag aagccaatca gcgtcgccac gactcccgac tataaagtcc ccatccggac      180
tcaagaagtt ctcaggactc agagg                                            205
```

<210> SEQ ID NO 5
<211> LENGTH: 252
<212> TYPE: DNA
<213> ORGANISM: Homo sapiens

<400> SEQUENCE: 5

```
aggccccgag gcggtgtctg gggttggaag gctcagtatt gagaattccc catctcccca       60
gagtttctct ttctctccca acccgtgtca ggtccttcat cctggatact cataacgcgg      120
ccccatttct cactcccatt gggcgtcgcg tttctagaga agccaatcag tgtcgccgca      180
gttcccaggt tctaaagtcc cacgcacccc gcgggactca tattttttccc agacgcggag    240 gttggggtca tg                                                          252
```

<210> SEQ ID NO 6
<211> LENGTH: 192
<212> TYPE: DNA
<213> ORGANISM: Homo sapiens

<400> SEQUENCE: 6

```
aacatcacga gactctaaga aaaggaaact gaaaacggga aagtccctct ctctaacctg       60
gcactgcgtc gctggcttgg agacaggtga cggtccctgc gggccttgtc ctgattggct      120
```

```
gggcacgcgt ttaatataag tggaggcgtc gcgctggcgg gcattcctga agctgacagc    180
attcgggccg ag                                                        192
```

<210> SEQ ID NO 7
<211> LENGTH: 1062
<212> TYPE: DNA
<213> ORGANISM: Human T-cell lymphotropic virus

<400> SEQUENCE: 7

```
atggcccact cccagggtt tggacagagt cttcttttcg datacccagt ctacgtgttt    60
ggagactgtg tacaaggcga ctggtgcccc atctctgggg gactatgttc ggcccgccta   120
catcgtcacg ccctactggc cacctgtcca gagcatcaga tcacctggga ccccatcgat   180
ggacgcgtta tcggctcagc tctacagttc cttatccctc gactccctc cttccccacc   240 cagagaacct ctaagaccct taaggtcctt accccgccaa tcactcatac aaccccaac    300 attccacct cctcctcca ggccatgcgc aaatactccc ccttccgaaa tggatacatg      360
gaacccaccc ttgggcagca cctcccaacc ctgtctttc cagacccccg actccggccc    420
caaaacctgt acaccctctg ggaaggtctcc gttgtctgca tgtacctcta ccagctttcc  480 cccccatca cctggcccct cctgccccat gtgatttttt gccaccccgg ccagctcggg    540
gccttcctca ccaatgttcc ctacaaacga atagaaaaac tcctctataa aatttccctt    600
accacagggg ccctaataat tctacccgag gactgtttgc ccaccaccct tttccagcct    660
gctagggcac ccgtcacgct gacagcctgg caaaacggcc tccttccgtt ccactcaacc    720
ctcaccactc caggccttat ttggacattt accgatggca cgcctatgat ttccgggccc    780
tgccctaaag atggccagcc atctttagta ctacagtcct cctcctttat atttcacaaa    840
tttcaaacca aggcctacca ccctcattt ctactctcac acggcctcat acagtactct    900
tcctttcata atttgcatct cctattgaa gaatacacca acatcccat ttctctactt      960 tttaacgaaa aagaggcaga tgacaatgac catgagcccc aaatatcccc cggggcttta  1020
gagcctctca gtgaaaaaca tttccgtgaa acagaagtct ga                      1062
```

<210> SEQ ID NO 8
<211> LENGTH: 849
<212> TYPE: DNA
<213> ORGANISM: Artificial Sequence
<220> FEATURE:
<223> OTHER INFORMATION: Synthetic Tax antigen

<400> SEQUENCE: 8

```
atggcccact cccccggctt tggccagagc ctgctgttcg ctacccccgt gtacgtgttc    60
ggcgactgcg tggacggcag agtgatcggc agcgccctgc agttcctgat ccccagactg   120
cccagcttcc ccacccagcg gaccagcaag accctgaagg tgctgacccc cccatcacc    180 cacaccaccc caatatcccc ccagcttc ctgcaggcca tgcggaagta cagccccttc      240
cggaacggct acatggaacc caccctgggc cagcatctgc ccaccctgag cttccccgat    300
cctggcctgc ggccccagaa cctgtatacc ctgtgggcg cagcgtcgt gtgcatgtac    360 ctgtaccagc tgagccctcc tatcacctgg ccctgctgc ccacgtgat cttttgccac    420 cctggacagc tgggcgcctt cctgaccaac gtgccctaca gcggatcga aagctgctg    480 tacaagatca gcctgaccac aggcgccctg atcatcctgc ccgaggactg cctgcccacc    540 acctgttc agcccgccag agcccctgtg acctgaccg cctggcagaa cggcctgctg      600
```

```
ccctteccaca gcaccctgac caccectggc ctgatctgga ccttcaccga cggcaccccc    660
atgatcagcg ccccctgccc taaggacggc cagcctagcc tggtgctgca gagcagcagc    720
ttcatcttcc acaagttcca gaccaaggcc taccacccca gctttctgct gagccacggc    780
ctgatccagt actccagctt ccacaacctg catctgctgt tcgaagagta caccaacatc    840
cccatctcc                                                            849
```

<210> SEQ ID NO 9
<211> LENGTH: 621
<212> TYPE: DNA
<213> ORGANISM: Human T-cell lymphotropic virus

<400> SEQUENCE: 9

```
atggcggcct cagggctgtt tcgatgcttg cctgtgtcat gcccggagga cctgctggtg     60
gaggaattgg tggacgggct attatccttg gaggaagagt taaaggacaa ggaggaggag    120
aaagctgtgc ttgacggttt gctatcctta gaagaggaaa gccgcggccg gctgcgacgg    180
ggccctccag gggagaaagc gccacctcgc ggggaaacgc atcgtgatcg gcagcgacgg    240
gctgaggaga agaggaagcg aaaaaaagag cgggagaaag aggaggaaaa gcagattgct    300
gagtatttga aaggaagga agaggagaag gcacggcgca ggaggcgggc ggagaagaag    360
gccgctgacg tcgccaggag gaagcaggaa gagcaggagc gccgtgagcg caagtggaga    420
caaggggctg agaaggcgaa acagcatagt gctaggaaag aaaaaatgca ggagttgggg    480
attgatggct atactagaca gttggaaggc gaggtggagt ccttggaggc tgaacggagg    540
aagttgctgc aggagaagga ggatttgatg gagaggtta attattggca ggggaggctg    600
gaggcgatgt ggttgcaata a                                              621
```

<210> SEQ ID NO 10
<211> LENGTH: 357
<212> TYPE: DNA
<213> ORGANISM: Artificial Sequence
<220> FEATURE:
<223> OTHER INFORMATION: Synthetic HBZ antigen

<400> SEQUENCE: 10

```
atgctgttca gatgcctgcc cgtgtcctgc cccgaggacc tgctggtgga agaactggtg     60
gacggcctgc tgagcctgga agaggaactg aaggacaaag aggaagagaa ggccgtcctg    120
gatggcctgc tgtctctgga agaagagagc cggggcagac tgcggagagg ccctcctggc    180
gagaaagccc cccctagagg cgagacacac cgggacagac agagaagggc cgaggaagag    240
cgcgagaaag aagaggaaaa gcagatcgcc gagtacctga gcggaaagag agaagagaaa    300
gcccgcgaga gaaagccgc cgacgtggcc agacggaagc aggaagaaca ggaacgg       357
```

<210> SEQ ID NO 11
<211> LENGTH: 459
<212> TYPE: DNA
<213> ORGANISM: Homo sapiens

<400> SEQUENCE: 11

```
atgcccaaga cccgtcggag gccccgccga tcccaaagaa aaagacctcc aacaccatgg     60
cagcctcctc cgttcagcct ccaaggactc cacctcgcct ccaactgtc tagtatagcc    120 atcaatcccc aactcctgca ttttttcttt cctagcacta tgctgtttcg ccttctcagc    180
cccttgtctc cacttgcgct cacggcgctc ctgctcttcc tgcttcctcc tagcgacgtc    240
agcggccttc ttctccgccc gcctcctgcg ccgtgccttc tcctcttcct tccttttcaa    300
```

```
atactcagcg gtctgctttt cctcctcttt ctcccgctct ttttttcgct tcctcttctc    360
ctcagcccgt cgctgccgat cacgatgcgt tccccgcgga ggtggcgctt tctcccctgg    420
agggccccgt cgcagccggc cgcggctttc ctcttctaa                           459
```

<210> SEQ ID NO 12
<211> LENGTH: 201
<212> TYPE: DNA
<213> ORGANISM: Artificial Sequence
<220> FEATURE:
<223> OTHER INFORMATION: Synthetic p12I antigen
<400> SEQUENCE: 12

```
atgcccaaga ccagaaggcg gcccagaaga agccagagaa agaggccccc taccccctgg    60
cagcctcctc cattcagtct gcagggcctg cacctggcct tccagctgag cagcattgcc   120
atcaaccccc agctgctgca cttcttcttc ccttccacca tgctgttccg gctgctgagc   180
cctctgtctc ctctggccct g                                              201
```

<210> SEQ ID NO 13
<211> LENGTH: 726
<212> TYPE: DNA
<213> ORGANISM: Homo sapiens
<400> SEQUENCE: 13

```
atggcactat gctgtttcgc cttctcagcc ccttgtctcc acttgcgctc acggcgctcc    60
tgctcttcct gcttcctcct agcgacgtca gcggccttct tctccgcccg cctcctgcgc   120
cgtgccttct cctcttcctt ccttttcaaa tactcagcgg tctgcttttc ctcctctttc   180
tcccgctctt ttttcgcttc ctcttctcc tcagcccgtc gctgccgatc acgatgcgtt   240
tccccgcgag gtggcgcttt ctcccctgga gggccccgtc gcagccggcc gcggctttcc   300
tcttctaagg atagcaaacc gtcaagcaca gcttcctcct cctccttgtc ctttaactct   360
tcctccaagg ataatagccc gtccaccaat tcctccacca gcaggtcctc cgggcatgac   420
acaggcaagc atcgaaacag ccctgcagat acaaagttaa ccatgcttat tatcagccca   480
cttcccaggg tttggacaga gtcttctttt cggatacccca gtctacgtgt ttggagactg   540
tgtacaaggc gactggtgcc ccatctctgg gggactatgt tcggcccgcc tacatcgtca   600
cgccctactg gccacctgtc cagagcatca gatcacctgg accccatcg atggacgcgt   660 tatcggctca gctctacagt tccttatccc tcgactcccc tccttcccca cccagagaac   720
ctctaa                                                              726
```

<210> SEQ ID NO 14
<211> LENGTH: 90
<212> TYPE: DNA
<213> ORGANISM: Artificial Sequence
<220> FEATURE:
<223> OTHER INFORMATION: Synthetic P30II antigen
<400> SEQUENCE: 14

```
gccaccagcg ccgccttttt tagcgccaga ctgctgcgga gagccctgac catgctgatc    60
atcagccccc tgcccagagt gtggaccgag                                      90
```

<210> SEQ ID NO 15
<211> LENGTH: 1212
<212> TYPE: DNA
<213> ORGANISM: Artificial Sequence
<220> FEATURE:

<223> OTHER INFORMATION: Synthetic TAX-HBZ

<400> SEQUENCE: 15

```
atggcccact tccccggctt tggccagagc ctgctgttcg ctaccccgt gtacgtgttc      60
ggcgactgcg tggacggcag agtgatcggc agcgccctgc agttcctgat ccccagactg     120
cccagcttcc ccacccagcg gaccagcaag accctgaagg tgctgacccc ccccatcacc    180
cacaccaccc ccaatatccc ccccagcttc ctgcaggcca tgcggaagta cagcccttc     240
cggaacggct acatggaacc caccctgggc cagcatctgc ccaccctgag cttccccgat    300
cctggcctgc ggccccagaa cctgtatacc ctgtggggcg cagcgtcgt gtgcatgtac     360
ctgtaccagc tgagccctcc tatcacctgg cccctgctgc ccacgtgat cttttgccac     420
cctggacagc tgggcgcctt cctgaccaac gtgccctaca gcggatcga aagctgctg      480
tacaagatca gcctgaccac aggcgccctg atcatcctgc cgaggactg cctgcccacc     540
accctgtttc agcccgccag agcccctgtg accctgaccg cctggcagaa cggcctgctg    600
ccctccaca gcaccctgac caccctggc ctgatctgga ccttcaccga cggcaccccc      660
atgatcagcg gcccctgccc taaggacggc cagcctagcc tggtgctgca gagcagcagc    720
ttcatcttcc acaagttcca gaccaaggcc taccaccca gctttctgct gagccacggc    780
ctgatccagt actccagctt ccacaacctg catctgctgt cgaagagta caccaacatc     840
cccatctcca tgctgttcag atgcctgccc gtgtcctgcc ccgaggacct gctggtggaa    900
gaactggtgg acggcctgct gagcctggaa gaggaactga aggacaaaga ggaagagaag   960
gccgtcctgg atggcctgct gtctctggaa gaagagagcc gggcagact gcggagaggc    1020
cctcctggcg agaaagcccc cctagaggc gagacacacc gggacagaca gagaagggcc   1080
gaggaagagc gcgagaaaga gaggaaaag cagatcgccg agtacctgaa gcggaaagaa   1140
gaagagaaag cccgcgagaa aaagccgcc gacgtggcca gacggaagca ggaagaacag    1200
gaacggtgat ga                                                        1212
```

<210> SEQ ID NO 16
<211> LENGTH: 1212
<212> TYPE: DNA
<213> ORGANISM: Artificial Sequence
<220> FEATURE:
<223> OTHER INFORMATION: Synthetic HBZ-TAX CO

<400> SEQUENCE: 16

```
atgctgttca gatgcctgcc cgtgtcctgc cccgaggacc tgctggtgga agaactggtg      60
gacggcctgc tgagcctgga agaggaactg aaggacaaag aggaagagaa ggccgtcctg    120
gatggcctgc tgtctctgga agaagagagc ggggcagac tgcggagagg ccctcctggc     180
gagaaagccc ccctagaggc gagacacac cgggacagac agagaagggc cgaggaagag    240
cgcgagaaag aagaggaaaa gcagatcgcc gagtacctga gcggaaaga agaagagaaa    300
gcccgcgaga gaaagccgc cgacgtggcc agacggaagc aggaagaaca ggaacggatg    360
gcccacttcc ccggctttgg ccagagcctg ctgttcggct accccgtgta cgtgttcggc    420
gactgcgtgg acggcagagt gatcggcagc gccctgcagt tcctgatccc cagactgccc    480
agcttcccca cccagcggac cagcaagacc ctgaaggtgc tgaccccccc catcacccac    540
caccccca atatccccc cagcttcctg caggccatgc ggaagtacag ccccttccgg      600
aacggctaca tggaacccac cctgggccag catctgccca ccctgagctt ccccgatcct    660
ggcctgcggc cccagaacct gtataccctg tggggcggca gcgtcgtgtg catgtacctg    720
```

```
taccagctga gccctcctat cacctggccc ctgctgcccc acgtgatctt ttgccaccct      780
ggacagctgg gcgccttcct gaccaacgtg ccctacaagc ggatcgagaa gctgctgtac      840
aagatcagcc tgaccacagg cgccctgatc atcctgcccg aggactgcct gcccaccacc      900
ctgtttcagc ccgccagagc ccctgtgacc ctgaccgcct ggcagaacgg cctgctgccc      960
ttccacagca ccctgaccac ccctggcctg atctggacct tcaccgacgg cacccccatg     1020
atcagcggcc cctgccctaa ggacggccag cctagcctgg tgctgcagag cagcagcttc     1080
atcttccaca gttccagac caaggcctac caccccagct ttctgctgag ccacggcctg     1140
atccagtact ccagcttcca caacctgcat ctgctgttcg aagagtacac caacatcccc     1200
atctcctgat ga                                                         1212

<210> SEQ ID NO 17
<211> LENGTH: 1296
<212> TYPE: DNA
<213> ORGANISM: Artificial Sequence
<220> FEATURE:
<223> OTHER INFORMATION: Synthetic TAX-2A-HBZ

<400> SEQUENCE: 17
atggcccact tccccggctt tggccagagc ctgctgttcg gctaccccgt gtacgtgttc       60
ggcgactgcg tggacggcag agtgatcggc agcgccctgc agttcctgat ccccagactg      120
cccagcttcc ccacccagcg gaccagcaag acctgaagg tgctgacccc ccccatcacc      180
cacaccaccc ccaatatccc ccccagcttc ctgcaggcca tgcggaagta cagcccctcc     240
cggaacggct acatggaacc caccctgggc cagcatctgc ccaccctgag cttccccgat      300
cctggcctgc ggccccagaa cctgtatacc ctgtggggcg cagcgtcgt gtgcatgtac      360 ctgtaccagc tgagccctcc tatcacctgg ccctgctgc ccacgtgat ctttgccac       420 cctggacagc tgggcgcctt cctgaccaac gtgccctaca gcggatcga agctgctg       480 tacaagatca gcctgaccac aggcgccctg atcatcctgc cgaggactg cctgcccacc      540 accctgtttc agcccgccag agcccctgtg accctgaccg cctggcagaa cggcctgctg      600
cccttccaca gcaccctgac caccctggc ctgatctgga ccttcaccga cggcaccccc      660
atgatcagcg gcccctgccc taaggacggc cagcctagcc tggtgctgca gagcagcagc      720
ttcatcttcc acaagttcca gaccaaggcc taccacccca gctttctgct gagccacggc      780
ctgatccagt actccagctt ccacaacctg catctgctgt tcgaagagta caccaacatc      840
cccatctcca cgcgtgcccc tgtgaagcag accctgaatt cgatctgct gaagctggcc      900 ggcgacgtgg agtctaatcc tggcccaact agtatgctgt tcagatgcct gcccgtgtcc      960
tgccccgagc cctgctggt ggaagaactg gtggacggcc tgctgagcct ggaagaggaa     1020
ctgaaggaca agaggaaga aaggccgtc ctggatggcc tgctgtctct ggaagaagag     1080
agccggggca gactgcggag aggccctcct ggcgagaag ccccccctag aggcgagaca     1140
caccgggaca gacagagaag ggccgaggaa gagcgcgaga agaagagga aaagcagatc     1200 gccgagtacc tgaagcggaa agaagaagag aaagcccgcg agaagaaagc cgccgacgtg     1260
gccagacgga agcaggaaga acaggaacgg tgatga                              1296

<210> SEQ ID NO 18
<211> LENGTH: 1296
<212> TYPE: DNA
<213> ORGANISM: Artificial Sequence
<220> FEATURE:
```

<223> OTHER INFORMATION: Synthetic HBZ-2A-TAX

<400> SEQUENCE: 18

```
atgctgttca gatgcctgcc cgtgtcctgc cccgaggacc tgctggtgga agaactggtg      60
gacggcctgc tgagcctgga agaggaactg aaggacaaag aggaagagaa ggccgtcctg     120
gatggcctgc tgtctctgga agaagagagc cggggcagac tgcggagagg ccctcctggc     180
gagaaagccc cccctagagg cgagacacac cgggacagac agagaagggc cgaggaagag     240
cgcgagaaag aagaggaaaa gcagatcgcc gagtacctga gcggaaaga agaagagaaa     300
gcccgcgaga gaaagccgc cgacgtggcc agacggaagc aggaagaaca ggaacggacg     360
cgtgcccctg tgaagcagac cctgaatttc gatctgctga gctggccgg cgacgtggag     420
tctaatcctg gcccaactag tatggcccac ttccccggct ttggccagag cctgctgttc     480
ggctaccccg tgtacgtgtt cggcgactgc gtggacggca gagtgatcgg cagcgccctg     540
cagttcctga tccccagact gcccagcttc cccacccagc ggaccagcaa gaccctgaag     600
gtgctgaccc cccccatcac ccacaccacc cccaatatcc cccccagctt cctgcaggcc     660
atgcggaagt acagccccct tccggaacgg tacatggaac ccaccctggg ccagcatctg     720
cccaccctga gcttccccga tcctggcctg cggcccagaa acctgtatac cctgtggggc     780
ggcagcgtcg tgtgcatgta cctgtaccag ctgagccctc ctatcacctg gcccctgctg     840
ccccacgtga tcttttgcca ccctggacag ctgggcgcct tcctgaccaa cgtgccctac     900
aagcggatcg agaagctgct gtacaagatc agcctgacca caggcgccct gatcatcctg     960
cccgaggact gcctgccac caccctgttt cagcccgcca gagcccctgt gacccctgacc    1020
gcctggcaga acggcctgct gcccttccac agcaccctga ccaccctgg cctgatctgg    1080
accttcaccg acggcacccc catgatcagc ggcccctgcc taaggacgg ccagcctagc    1140
ctggtgctgc agagcagcag cttcatcttc cacaagttcc agaccaaggc ctaccacccc    1200
agctttctgc tgagccacgg cctgatccag tactccagct ccacaacct gcatctgctg    1260
ttcgaagagt acaccaacat ccccatctcc tgatga                              1296
```

<210> SEQ ID NO 19
<211> LENGTH: 291
<212> TYPE: DNA
<213> ORGANISM: Artificial Sequence
<220> FEATURE:
<223> OTHER INFORMATION: Synthetic p12Ip30II

<400> SEQUENCE: 19

```
atgcccaaga ccagaaggcg gcccagaaga agccagagaa agaggccccc taccccctgg      60
cagcctcctc cattcagtct gcagggcctg cacctggcct tccagctgag cagcattgcc     120
atcaaccccc agctgctgca cttcttcttc ccttccacca tgctgttccg gctgctgagc     180
cctctgtctc tctgggccct ggccaccagc gccgcctttt ttagcgccag actgctgcgg     240
agagccctga ccatgctgat catcagcccc ctgcccagag tgtggaccga g              291
```

<210> SEQ ID NO 20
<211> LENGTH: 1503
<212> TYPE: DNA
<213> ORGANISM: Artificial Sequence
<220> FEATURE:
<223> OTHER INFORMATION: Synthetic p12Ip30II-Tax-HBZ

<400> SEQUENCE: 20

```
atgcccaaga ccagaaggcg gcccagaaga agccagagaa agaggccccc taccccctgg      60
```

```
cagcctcctc cattcagtct gcagggcctg cacctggcct tccagctgag cagcattgcc    120
atcaaccccc agctgctgca cttcttcttc ccttccacca tgctgttccg gctgctgagc    180
cctctgtctc ctctggccct ggccaccagc gccgcctttt ttagcgccag actgctgcgg    240
agagccctga ccatgctgat catcagcccc ctgcccagag tgtggaccga gatggcccac    300
ttccccggct ttggccagag cctgctgttc ggctacccg tgtacgtgtt cggcgactgc    360
gtggacggca gagtgatcgg cagcgccctg cagttcctga tccccagact gcccagcttc    420
cccacccagc ggaccagcaa gaccctgaag gtgctgaccc ccccatcac ccacaccacc    480 cccaatatcc cccccagctt cctgcaggcc atgcggaagt acagccccett ccggaacggc    540 tacatggaac ccaccctggg ccagcatctg cccaccctga gcttccccga tcctggcctg    600
cggccccaga acctgtatac cctgtggggc ggcagcgtcg tgtgcatgta cctgtaccag    660
ctgagccctc ctatcacctg gccctgctg ccccacgtga tcttttgcca ccctggacag    720
ctgggcgcct tcctgaccaa cgtgccctac aagcggatcg agaagctgct gtacaagatc    780
agcctgacca caggcgccct gatcatcctg cccgaggact gcctgcccac caccctgttt    840
cagcccgcca gagcccctgt gaccctgacc gcctggcaga acggcctgct gcccttccac    900
agcaccctga ccacccctgg cctgatctgg accttcaccg acggcacccc catgatcagc    960 ggccctgcc ctaaggacgg ccagcctagc ctggtgctgc agagcagcag cttcatcttc    1020
cacaagttcc agaccaaggc ctaccacccc agctttctgc tgagccacgg cctgatccag    1080
tactccagct ccacaacct gcatctgctg ttcgaagagt acaccaacat ccccatctcc    1140
atgctgttca gatgcctgcc cgtgtcctgc cccgaggacc tgctggtgga agaactggtg    1200
gacggcctgc tgagcctgga agaggaactg aaggacaaag aggaagagaa ggccgtcctg    1260
gatggcctgc tgtctctgga agaagagagc cggggcagac tgcggagagg ccctcctggc    1320
gagaaagccc ccctagagg cgagacacac cgggacagac agagaagggc cgaggaagag    1380
cgcgagaaag aagaggaaaa gcagatcgcc gagtacctga gcggaaaaga agaagagaaa    1440
gcccgcgaga gaaagccgc cgacgtggcc agacggaagc aggaagaaca ggaacggtga    1500
tga                                                                  1503
```

<210> SEQ ID NO 21
<211> LENGTH: 1503
<212> TYPE: DNA
<213> ORGANISM: Artificial Sequence
<220> FEATURE:
<223> OTHER INFORMATION: Synthetic Tax-HBZ-p12Ip30II

<400> SEQUENCE: 21

```
atggcccact tccccggctt tggccagagc ctgctgttcg gctacccgt gtacgtgttc     60 ggcgactgcg tggacggcag agtgatcggc agcgccctgc agttcctgat ccccagactg    120
cccagcttcc ccacccagcg gaccagcaag accctgaagg tgctgacccc ccccatcacc    180
cacaccaccc ccaatatccc cccagcttc ctgcaggcca tgcggaagta cagccccttc    240
cggaacggct acatggaacc caccctgggc cagcatctgc ccaccctgag cttccccgat    300
cctggcctgc ggccccagaa cctgtatacc ctgtggggcg gcagcgtcgt gtgcatgtac    360
ctgtaccagc tgagccctcc tatcacctgg ccctgctgc ccacgtgat cttttgccac    420 cctggacagc tgggcgcctt cctgaccaac gtgccctaca agcggatcga gaagctgctg    480
tacaagatca gcctgaccac aggcgccctg atcatcctgc ccgaggactg cctgcccacc    540
```

-continued

| | |
|---|---|
| accctgtttc agcccgccag agcccctgtg accctgaccg cctggcagaa cggcctgctg | 600 |
| cccttccaca gcaccctgac cacccctggc ctgatctgga ccttcaccga cggcaccccc | 660 |
| atgatcagcg gcccctgccc taaggacggc cagcctagcc tggtgctgca gagcagcagc | 720 |
| ttcatcttcc acaagttcca gaccaaggcc taccacccca gctttctgct gagccacggc | 780 |
| ctgatccagt actccagctt ccacaacctg catctgctgt tcgaagagta caccaacatc | 840 |
| cccatctcca tgctgttcag atgcctgccc gtgtcctgcc ccgaggacct gctggtggaa | 900 |
| gaactggtgg acggcctgct gagcctggaa gaggaactga aggacaaaga ggaagagaag | 960 |
| gccgtcctgg atggcctgct gtctctggaa gaagagagcc ggggcagact gcggagaggc | 1020 |
| cctcctggcg agaaagcccc ccctagaggc gagacacacc gggacagaca gagaagggcc | 1080 |
| gaggaagagc gcgagaaaga gaggaaaaga cagatcgccg agtacctgaa gcggaaagaa | 1140 |
| gaagagaaag cccgcgagaa gaaagccgcc gacgtggcca gacggaagca ggaagaacag | 1200 |
| gaacggtgat gaatgcccaa gaccagaagg cggcccagaa gaagccagag aaagaggccc | 1260 |
| cctacccccct ggcagcctcc tccattcagt ctgcagggcc tgcacctggc cttccagctg | 1320 |
| agcagcattg ccatcaaccc ccagctgctg cacttcttct tcccttccac catgctgttc | 1380 |
| cggctgctga gccctctgtc tcctctggcc ctggccacca gcgccgcctt ttttagcgcc | 1440 |
| agactgctgc ggagagccct gaccatgctg atcatcagcc ccctgcccag agtgtggacc | 1500 |
| gag | 1503 |

<210> SEQ ID NO 22
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 22
ggatccgcca ccatggccca ctttccagg                                    29

<210> SEQ ID NO 23
<211> LENGTH: 28
<212> TYPE: DNA
<213> ORGANISM: Artificial Sequence
<220> FEATURE:
<223> OTHER INFORMATION: Synthetic PCR Primer

<400> SEQUENCE: 23
gctgataggg atgttggtgt actcttcg                                     28

<210> SEQ ID NO 24
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 24
ggatccgcca ccatgctgtt cagatgcct                                    29

<210> SEQ ID NO 25
<211> LENGTH: 28
<212> TYPE: DNA
<213> ORGANISM: Artificial Sequence
<220> FEATURE:
<223> OTHER INFORMATION: Synthetic PCR Primer

<400> SEQUENCE: 25

-continued gcgttcctgt tcttcctgct tccgtctg                                      28

<210> SEQ ID NO 26
<211> LENGTH: 28
<212> TYPE: DNA
<213> ORGANISM: Artificial Sequence
<220> FEATURE:
<223> OTHER INFORMATION: Synthetic PCR Primer

<400> SEQUENCE: 26
ggatccgcca ccatggccca ctttccag                                      28

<210> SEQ ID NO 27
<211> LENGTH: 28
<212> TYPE: DNA
<213> ORGANISM: Artificial Sequence
<220> FEATURE:
<223> OTHER INFORMATION: Synthetic PCR Primer

<400> SEQUENCE: 27
gcgttcctgt tcttcctgct tccgtctg                                      28

<210> SEQ ID NO 28
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 28
ggatccgcca ccatgcccaa gaccagaag                                     29

<210> SEQ ID NO 29
<211> LENGTH: 27
<212> TYPE: DNA
<213> ORGANISM: Artificial Sequence
<220> FEATURE:
<223> OTHER INFORMATION: Synthetic PCR Primer

<400> SEQUENCE: 29
ctcggtccac actctgggca gggggct                                       27

<210> SEQ ID NO 30
<211> LENGTH: 45
<212> TYPE: DNA
<213> ORGANISM: Artificial Sequence
<220> FEATURE:
<223> OTHER INFORMATION: Synthetic PCR Primer

<400> SEQUENCE: 30
agagtacacc aacatcccta tcagcatgct gttcagatgc ctgcc                   45

<210> SEQ ID NO 31
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 31
ctcgagttat cagcgttcct gttcttcctg                                    30

<210> SEQ ID NO 32
<211> LENGTH: 45
<212> TYPE: DNA

```
<213> ORGANISM: Artificial Sequence
<220> FEATURE:
<223> OTHER INFORMATION: Synthetic PCR Primer

<400> SEQUENCE: 32
acggaagcag gaagaacagg aacgcatggc ccactttcca ggctt        45

<210> SEQ ID NO 33
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 33
ctcgagtcat cagctgatag ggatgttgg                          29

<210> SEQ ID NO 34
<211> LENGTH: 47
<212> TYPE: DNA
<213> ORGANISM: Artificial Sequence
<220> FEATURE:
<223> OTHER INFORMATION: Synthetic PCR Primer

<400> SEQUENCE: 34
gacggaagca ggaagaacag gaacgcatgc ccaagaccag aaggcgg      47

<210> SEQ ID NO 35
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 35
ctcgagtcat cactcggtcc acactctggg                         30

<210> SEQ ID NO 36
<211> LENGTH: 47
<212> TYPE: DNA
<213> ORGANISM: Artificial Sequence
<220> FEATURE:
<223> OTHER INFORMATION: Synthetic PCR Primer

<400> SEQUENCE: 36 cccctgccc agagtgtgga ccgagatggc ccactttcca ggctttg       47

<210> SEQ ID NO 37
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 37
ctcgagttat cagcgttcct gttcttcctg                         30

<210> SEQ ID NO 38
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 38
ctcgagttat cagcgttcct gttcttcctg                         30
```

<210> SEQ ID NO 39
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 39
ctcgagttat cagcgttcct gttcttcctg                                    30

<210> SEQ ID NO 40
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 40
ggatccgcca ccatgctgtt cagatgcct                                     29

<210> SEQ ID NO 41
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 41
ctcgagtcat cagctgatag ggatgttgg                                     29

<210> SEQ ID NO 42
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 42
ggatccgcca ccatggccca ctttccagg                                     29

<210> SEQ ID NO 43
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 43
ctcgagtcat cactcggtcc acactctggg                                    30

<210> SEQ ID NO 44
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 44
ggatccgcca ccatgcccaa gaccagaag                                     29

<210> SEQ ID NO 45
<211> LENGTH: 30
<212> TYPE: DNA
<213> ORGANISM: Artificial Sequence
<220> FEATURE:

```
<223> OTHER INFORMATION: Synthetic PCR Primer

<400> SEQUENCE: 45
ctcgagttat cagcgttcct gttcttcctg                               30

<210> SEQ ID NO 46
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 46
ggatccgcca ccatggccca ctttccagg                                29

<210> SEQ ID NO 47
<211> LENGTH: 59
<212> TYPE: DNA
<213> ORGANISM: Artificial Sequence
<220> FEATURE:
<223> OTHER INFORMATION: Synthetic PCR Primer

<400> SEQUENCE: 47
attcagggtc tgcttcacag gggcacgcgt gctgataggg atgttggtgt actcttcga   59

<210> SEQ ID NO 48
<211> LENGTH: 55
<212> TYPE: DNA
<213> ORGANISM: Artificial Sequence
<220> FEATURE:
<223> OTHER INFORMATION: Synthetic PCR Primer

<400> SEQUENCE: 48
gacgtggagt ctaatcctgg cccaactagt atgctgttca gatgcctgcc cgtgt       55

<210> SEQ ID NO 49
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 49
ctcgagttat cagcgttcct gttcttcctg                               30

<210> SEQ ID NO 50
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 50
ggatccgcca ccatgctgtt cagatgcct                                29

<210> SEQ ID NO 51
<211> LENGTH: 58
<212> TYPE: DNA
<213> ORGANISM: Artificial Sequence
<220> FEATURE:
<223> OTHER INFORMATION: Synthetic PCR Primer

<400> SEQUENCE: 51
attcagggtc tgcttcacag gggcacgcgt gcgttcctgt tcttcctgct tccgtctg    58
```

```
<210> SEQ ID NO 52
<211> LENGTH: 55
<212> TYPE: DNA
<213> ORGANISM: Artificial Sequence
<220> FEATURE:
<223> OTHER INFORMATION: Synthetic PCR Primer

<400> SEQUENCE: 52
gacgtggagt ctaatcctgg cccaactagt atgcccact ttccaggctt tggcc        55

<210> SEQ ID NO 53
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 53
ctcgagtcat cagctgatag ggatgttgg                                     29

<210> SEQ ID NO 54
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 54
ggatccgcca ccatggccca ctttccagg                                     29

<210> SEQ ID NO 55
<211> LENGTH: 50
<212> TYPE: DNA
<213> ORGANISM: Artificial Sequence
<220> FEATURE:
<223> OTHER INFORMATION: Synthetic PCR Primer

<400> SEQUENCE: 55
gccggccagc ttcagcagat cgaaattcag ggtctgcttc acaggggcac              50

<210> SEQ ID NO 56
<211> LENGTH: 50
<212> TYPE: DNA
<213> ORGANISM: Artificial Sequence
<220> FEATURE:
<223> OTHER INFORMATION: Synthetic PCR Primer

<400> SEQUENCE: 56
ttcgatctgc tgaagctggc cggcgacgtg gagtctaatc ctggcccaac              50

<210> SEQ ID NO 57
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 57
ctcgagttat cagcgttcct gttcttcctg                                    30

<210> SEQ ID NO 58
<211> LENGTH: 29
<212> TYPE: DNA
<213> ORGANISM: Artificial Sequence
<220> FEATURE:
<223> OTHER INFORMATION: Synthetic PCR Primer
```

<400> SEQUENCE: 58
ggatccgcca ccatgctgtt cagatgcct                                    29

<210> SEQ ID NO 59
<211> LENGTH: 50
<212> TYPE: DNA
<213> ORGANISM: Artificial Sequence
<220> FEATURE:
<223> OTHER INFORMATION: Synthetic PCR Primer

<400> SEQUENCE: 59
gccggccagc ttcagcagat cgaaattcag ggtctgcttc acagggcac              50

<210> SEQ ID NO 60
<211> LENGTH: 50
<212> TYPE: DNA
<213> ORGANISM: Artificial Sequence
<220> FEATURE:
<223> OTHER INFORMATION: Synthetic PCR Primer

<400> SEQUENCE: 60
ttcgatctgc tgaagctggc cggcgacgtg gagtctaatc ctggcccaac             50

<210> SEQ ID NO 61
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 61
ctcgagtcat cagctgatag ggatgttgg                                    29

<210> SEQ ID NO 62
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 62
ggatccgcca ccatggccca ctttccagg                                    29

<210> SEQ ID NO 63
<211> LENGTH: 30
<212> TYPE: DNA
<213> ORGANISM: Artificial Sequence
<220> FEATURE:
<223> OTHER INFORMATION: Synthetic PCR Primer

<400> SEQUENCE: 63
ctcgagttat cagcgttcct gttcttcctg                                   30

<210> SEQ ID NO 64
<211> LENGTH: 29
<212> TYPE: DNA
<213> ORGANISM: Artificial Sequence
<220> FEATURE:
<223> OTHER INFORMATION: Synthetic PCR Primer

<400> SEQUENCE: 64
ggatccgcca ccatgctgtt cagatgcct                                    29

<210> SEQ ID NO 65
<211> LENGTH: 29

```
<212> TYPE: DNA
<213> ORGANISM: Artificial Sequence
<220> FEATURE:
<223> OTHER INFORMATION: Synthetic PCR Primer

<400> SEQUENCE: 65
ctcgagtcat cagctgatag ggatgttgg                                              29

<210> SEQ ID NO 66
<211> LENGTH: 499
<212> TYPE: PRT
<213> ORGANISM: Artificial Sequence
<220> FEATURE:
<223> OTHER INFORMATION: Synthetic HTLV-1 p12p30-Tax-HBZ fusion protein

<400> SEQUENCE: 66
```

Met Pro Lys Thr Arg Arg Pro Arg Arg Ser Gln Arg Lys Arg Pro
1               5                   10                  15

Pro Thr Pro Trp Gln Pro Pro Phe Ser Leu Gln Gly Leu His Leu
                20                  25                  30

Ala Phe Gln Leu Ser Ser Ile Ala Ile Asn Pro Gln Leu Leu His Phe
            35                  40                  45

Phe Phe Pro Ser Thr Met Leu Phe Arg Leu Leu Ser Pro Leu Ser Pro
50                  55                  60

Leu Ala Leu Ala Thr Ser Ala Ala Phe Ser Ala Arg Leu Leu Arg
65                  70                  75                  80

Arg Ala Leu Thr Met Leu Ile Ile Ser Pro Leu Pro Arg Val Trp Thr
                85                  90                  95

Glu Met Ala His Phe Pro Gly Phe Gly Gln Ser Leu Leu Phe Gly Tyr
                100                 105                 110

Pro Val Tyr Val Phe Gly Asp Cys Val Asp Gly Arg Val Ile Gly Ser
            115                 120                 125

Ala Leu Gln Phe Leu Ile Pro Arg Leu Pro Ser Phe Pro Thr Gln Arg
130                 135                 140

Thr Ser Lys Thr Leu Lys Val Leu Thr Pro Pro Ile Thr His Thr Thr
145                 150                 155                 160

Pro Asn Ile Pro Pro Ser Phe Leu Gln Ala Met Arg Lys Tyr Ser Pro
                165                 170                 175

Phe Arg Asn Gly Tyr Met Glu Pro Thr Leu Gly Gln His Leu Pro Thr
            180                 185                 190

Leu Ser Phe Pro Asp Pro Gly Leu Arg Pro Gln Asn Leu Tyr Thr Leu
        195                 200                 205

Trp Gly Gly Ser Val Val Cys Met Tyr Leu Tyr Gln Leu Ser Pro Pro
210                 215                 220

Ile Thr Trp Pro Leu Leu Pro His Val Ile Phe Cys His Pro Gly Gln
225                 230                 235                 240

Leu Gly Ala Phe Leu Thr Asn Val Pro Tyr Lys Arg Ile Glu Lys Leu
                245                 250                 255

Leu Tyr Lys Ile Ser Leu Thr Thr Gly Ala Leu Ile Ile Leu Pro Glu
            260                 265                 270

Asp Cys Leu Pro Thr Thr Leu Phe Gln Pro Ala Arg Ala Pro Val Thr
        275                 280                 285

Leu Thr Ala Trp Gln Asn Gly Leu Leu Pro Phe His Ser Thr Leu Thr
290                 295                 300

Thr Pro Gly Leu Ile Trp Thr Phe Thr Asp Gly Thr Pro Met Ile Ser
305                 310                 315                 320

```
Gly Pro Cys Pro Lys Asp Gly Gln Pro Ser Leu Val Leu Gln Ser Ser
                325                 330                 335

Ser Phe Ile Phe His Lys Phe Gln Thr Lys Ala Tyr His Pro Ser Phe
            340                 345                 350

Leu Leu Ser His Gly Leu Ile Gln Tyr Ser Ser Phe His Asn Leu His
        355                 360                 365

Leu Leu Phe Glu Glu Tyr Thr Asn Ile Pro Ile Ser Met Leu Phe Arg
    370                 375                 380

Cys Leu Pro Val Ser Cys Pro Glu Asp Leu Leu Val Glu Glu Leu Val
385                 390                 395                 400

Asp Gly Leu Leu Ser Leu Glu Glu Glu Leu Lys Asp Lys Glu Glu Glu
                405                 410                 415

Lys Ala Val Leu Asp Gly Leu Leu Ser Leu Glu Glu Glu Ser Arg Gly
            420                 425                 430

Arg Leu Arg Arg Gly Pro Pro Gly Glu Lys Ala Pro Pro Arg Gly Glu
        435                 440                 445

Thr His Arg Asp Arg Gln Arg Arg Ala Glu Glu Arg Glu Lys Glu
    450                 455                 460

Glu Glu Lys Gln Ile Ala Glu Tyr Leu Lys Arg Lys Glu Glu Lys
465                 470                 475                 480

Ala Arg Glu Lys Lys Ala Ala Asp Val Ala Arg Arg Lys Gln Glu Glu
                485                 490                 495

Gln Glu Arg

<210> SEQ ID NO 67
<211> LENGTH: 20
<212> TYPE: DNA
<213> ORGANISM: Artificial Sequence
<220> FEATURE:
<223> OTHER INFORMATION: Synthetic PCR primer

<400> SEQUENCE: 67
tggaggagga gatatgaggg                                             20

<210> SEQ ID NO 68
<211> LENGTH: 20
<212> TYPE: DNA
<213> ORGANISM: Artificial Sequence
<220> FEATURE:
<223> OTHER INFORMATION: Synthetic PCR Primer

<400> SEQUENCE: 68
ctgctgcact ataccagaca                                             20

<210> SEQ ID NO 69
<211> LENGTH: 27
<212> TYPE: DNA
<213> ORGANISM: Artificial Sequence
<220> FEATURE:
<223> OTHER INFORMATION: Synthetic Probe

<400> SEQUENCE: 69
aaccattagg agtagcaccc accaagg                                     27

<210> SEQ ID NO 70
<211> LENGTH: 22
<212> TYPE: DNA
<213> ORGANISM: Artificial Sequence
<220> FEATURE:
<223> OTHER INFORMATION: Synthetic PCR Primer
```

-continued

```
<400> SEQUENCE: 70
tcatcttcca caagttccag ac                                              22

<210> SEQ ID NO 71
<211> LENGTH: 24
<212> TYPE: DNA
<213> ORGANISM: Artificial Sequence
<220> FEATURE:
<223> OTHER INFORMATION: Synthetic PCR primer

<400> SEQUENCE: 71
gatagggatg ttggtgtact cttc                                            24
```